US011559346B2

(12) United States Patent
Henrywood

(10) Patent No.: US 11,559,346 B2
(45) Date of Patent: Jan. 24, 2023

(54) ELECTROSURGICAL NETWORK

(71) Applicant: CMR SURGICAL LIMITED, Cambridge (GB)

(72) Inventor: Ross Hamilton Henrywood, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 338 days.

(21) Appl. No.: 16/559,022

(22) Filed: Sep. 3, 2019

(65) Prior Publication Data
US 2019/0388137 A1 Dec. 26, 2019

Related U.S. Application Data

(63) Continuation-in-part of application No. PCT/GB2019/050560, filed on Feb. 28, 2019.

(30) Foreign Application Priority Data

Mar. 1, 2018 (GB) ..................................... 1803380

(51) Int. Cl.
*A61B 18/12* (2006.01)
*A61B 18/16* (2006.01)
(Continued)

(52) U.S. Cl.
CPC .......... *A61B 18/1206* (2013.01); *A61B 18/16* (2013.01); *A61B 34/30* (2016.02);
(Continued)

(58) Field of Classification Search
CPC ................ A61B 18/1206; A61B 18/16; A61B 18/00589; A61B 18/00601;
(Continued)

(56) References Cited

U.S. PATENT DOCUMENTS

2001/0029315 A1 10/2001 Sakurai et al.
2005/0251228 A1* 11/2005 Hamel ............. A61B 17/32002
607/60
(Continued)

FOREIGN PATENT DOCUMENTS

EP 2155096 A2 2/2010
GB 2571567 A 9/2019
(Continued)

OTHER PUBLICATIONS

Notification of Transmittal of the International Search Report and the Written Opinion of the International Searching Authority from corresponding PCT/GB2019/050560 dated May 3, 2019.
(Continued)

*Primary Examiner* — Daniel W Fowler
(74) *Attorney, Agent, or Firm* — Lando & Anastasi, LLP

(57) ABSTRACT

An electrosurgical system comprising: a plurality of electrosurgical connection units, each electrosurgical connection unit comprising an input port connectable to an electrosurgical channel and an output port connectable to an electrosurgical instrument, the electrosurgical connection unit configured to connect the input port to the output port; an electrosurgical network comprising a plurality of electrosurgical links that connect the input ports of the electrosurgical connection units to an electrosurgical channel; and a control unit configured to: receive information from a device indicating that the device has detected an electrosurgical generator connected to the electrosurgical channel, the device being one of the electrosurgical connection units and an electrosurgical output device connected to the electrosurgical channel; determine a location of the electrosurgical generator in the electrosurgical network based on the received information; and transmit one or more control signals to the electrosurgical connection units and/or one or more electrosurgical output devices connected to the elec-
(Continued)

trosurgical channel to cause the output port of a selected combination of electrosurgical connection units to be connected to the electrosurgical channel based on the determined location of the electrosurgical generator.

20 Claims, 20 Drawing Sheets

(51) Int. Cl.
  *A61B 34/30* (2016.01)
  *A61B 17/00* (2006.01)
  *A61B 18/00* (2006.01)
(52) U.S. Cl.
  CPC ............ *A61B 2017/00039* (2013.01); *A61B 2017/00057* (2013.01); *A61B 2017/00221* (2013.01); *A61B 2017/00477* (2013.01); *A61B 2018/00178* (2013.01); *A61B 2018/00589* (2013.01); *A61B 2018/00601* (2013.01); *A61B 2018/00607* (2013.01); *A61B 2018/00922* (2013.01); *A61B 2018/126* (2013.01); *A61B 2018/1253* (2013.01); *A61B 2018/1273* (2013.01)
(58) Field of Classification Search
  CPC ......... A61B 18/00922; A61B 18/1253; A61B 18/126; A61B 18/1273; A61B 18/1425; A61B 34/30
  See application file for complete search history.

(56) References Cited

U.S. PATENT DOCUMENTS

| | | | | |
|---|---|---|---|---|
| 2006/0095032 | A1* | 5/2006 | Jackson | A61B 5/4233 606/41 |
| 2009/0024120 | A1 | 1/2009 | Sartor | |
| 2009/0088774 | A1* | 4/2009 | Swarup | A61B 34/30 606/130 |
| 2009/0275940 | A1* | 11/2009 | Malackowski | A61B 18/1233 606/42 |
| 2010/0324548 | A1* | 12/2010 | Godara | A61B 18/1492 606/34 |
| 2011/0060329 | A1 | 3/2011 | Gilbert et al. | |
| 2012/0239020 | A1* | 9/2012 | Cunningham | A61B 18/1206 606/33 |
| 2013/0138097 | A1* | 5/2013 | Mathur | A61B 18/18 606/33 |
| 2014/0180272 | A1* | 6/2014 | Dachs, II | A61B 18/14 606/34 |
| 2017/0189095 | A1 | 7/2017 | Danziger et al. | |
| 2017/0202627 | A1* | 7/2017 | Sramek | A61B 34/30 |
| 2018/0021098 | A1* | 1/2018 | Hemphill | A61B 17/3421 606/41 |

FOREIGN PATENT DOCUMENTS

| | | |
|---|---|---|
| JP | 2015535193 A | 12/2015 |
| WO | 0137745 A1 | 5/2001 |
| WO | 02053048 A1 | 7/2002 |
| WO | 2014071184 A1 | 5/2014 |
| WO | 2017058617 A2 | 4/2017 |
| WO | 2017147106 A1 | 8/2017 |
| WO | 2018200254 A2 | 11/2018 |
| WO | 2018232360 A1 | 12/2018 |

OTHER PUBLICATIONS

United Kingdom Search Report from corresponding United Kingdom Application No. GB1803380.3 dated Aug. 16, 2018.
Indian Examination Report from corresponding Indian Application No. 2020027038760 dated Jun. 18, 2021.
United Kingdom Search Report from corresponding United Kingdom Application No. GB1912667.1 dated Jan. 22, 2020.
Japanese Notification of Reasons for Refusal from corresponding Japanese Application No. 2020-545528 dated Feb. 1, 2022.
United Kingdom Search Report from corresponding United Kingdom Application No. GB2200864.3.1 dated Mar. 31, 2022.
Indian Examination Report from corresponding Indian Application No. 202227020054 dated Aug. 23, 2022.
United Kingdom Search Report from corresponding United Kingdom Application No. GB2209815.6 dated Aug. 19, 2022.
United Kingdom Search Report from corresponding United Kingdom Application No. GB2209819.8 dated Aug. 19, 2022.

\* cited by examiner

ELECTROSURGICAL NETWORK

CROSS-REFERENCE TO RELATED APPLICATION

This application is a continuation-in-part of Patent Cooperation Treaty Application Serial No. PCT/GB2019/050560, entitled "ELECTROSURGICAL NETWORK", filed on Feb. 28, 2019, which claims the benefit of United Kingdom Patent Application No. 1803380.0, filed on Mar. 1, 2018. Each application referenced above is hereby incorporated herein by reference in its entirety for all purposes.

BACKGROUND

It is known to use robots for assisting and performing surgery. FIG. 1 illustrates a typical surgical robot 100 which comprises a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

A variety of surgical instruments are known, each adapted to perform a particular surgical function. FIG. 2 illustrates an example surgical instrument 200. The surgical instrument comprises a base 201 by means of which the surgical instrument connects to the robot arm. A shaft 202 extends between the base 201 and an articulation 203. The articulation 203 terminates in an end effector 204. The articulation 203 permits the end effector 204 to move relative to the shaft 202. It is desirable for at least two degrees of freedom to be provided to the motion of the electrosurgery end effector 204 by means of the articulation.

An electrosurgical instrument is a surgical instrument adapted to perform electrosurgery. As is known to those of skill in the art, electrosurgery is the passing of a high frequency (i.e. radio frequency) current through tissue to cause a desired effect (e.g. cutting the tissue or coagulating the tissue). In contrast to electrocautery which uses heat conduction from a probe heated by a direct current, electrosurgery uses radio frequency (RF) alternating current to heat the tissue by RF induced intracellular oscillation of ionized molecules that result in an intracellular temperature. Electrosurgical instruments typically receive the desired current from an electrosurgical generator (which may also be referred to as an electrosurgical end unit or ESU) via a cable.

Many surgical robot systems comprise multiple robot arms each of which can have an instrument attached thereto. For example, FIG. 3 illustrates an example surgical robot system 300 with three robot arms 302, 304, 306 each of which can have an instrument 308, 310, 312 attached thereto. To allow an electrosurgical instrument to be dynamically attached to any of the arms a surgical robot system may comprise a single electrosurgical generator which can be manually connected to one of the arms as appropriate. However, this makes the initial set-up of the system, and any dynamic shifting of an electrosurgical instrument from one arm to another, time consuming and prone to human error. Alternatively, a surgical robot system may comprise a plurality of electrosurgical generators wherein each generator is dedicated to an electrosurgical instrument connected to one of the arms. While such systems may resolve many of the problems with a system with a single electrosurgical generator, having multiple generators significantly increases the cost and complexity of the system.

Accordingly, there is a need for an alternative way of dynamically connecting an electrosurgical generator to an electrosurgical instrument attached to an arm of a multi-arm surgical robot.

The embodiments described below are provided by way of example only and are not limiting of implementations which solve any or all of the disadvantages of surgical robots with multiple arms to which an electrosurgical instrument can be attached.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

Described herein are electrosurgical systems comprising an electrosurgical network that connects a plurality of electrosurgical connection units (which are each connectable to an electrosurgical instrument) to one or more electrosurgical generators such that an electrosurgical signal generated by an electrosurgical generator can be controllably provided to any combination of electrosurgical connection units. Where the electrosurgical connection units are in physically separate locations of an operating room (e.g. one electrosurgical connection unit may be situated on a left side of a patient bed, and another electrosurgical connection unit may be situated on a right side of a patent bed) such electrosurgical systems allow an electrosurgical instrument to be located in a variety of locations throughout the operating room yet controlled/driven by any of the one or more electrosurgical generators. This allows the surgical instruments to be easily placed in different locations for different surgical procedures yet controlled by the same electrosurgical generator. Such electrosurgical systems also reduce reconfiguration errors that may be caused in systems where an electrosurgical instrument needs to be moved, during a surgical procedure, to a different location in the operating room on the fly.

A first aspect provides an electrosurgical system comprising: a plurality of electrosurgical connection units, each electrosurgical connection unit comprising an input port connectable to an electrosurgical channel and an output port connectable to an electrosurgical instrument, the electrosurgical connection unit configured to connect the input port to the output port; an electrosurgical network comprising a plurality of electrosurgical links that connect the input ports of the electrosurgical connection units to an electrosurgical channel via an electrosurgical output device; and a control unit configured to transmit one or more control signals to the electrosurgical connection units and/or the electrosurgical output device to cause the output port of a selected combination of electrosurgical connection units to be connected to the electrosurgical channel.

Each electrosurgical connection unit further comprises a switching unit between the input port and the output port, the switching unit configured to controllably connect the input port to the output port in response to a control signal.

The one or more control signals transmitted by the control unit may cause a selected combination of electrosurgical links to be active and all other electrosurgical links to be inactive.

The electrosurgical links may connect at least two of the electrosurgical connection units to the electrosurgical channel in a daisy chain configuration.

At least one electrosurgical connection unit may further comprises a second output port connected to the input port of another electrosurgical connection unit via an electrosurgical link, the at least one electrosurgical connection unit configured to electrically connect the input port to the second output port.

The at least one electrosurgical connection unit may further comprise a switching unit situated between the input port and the second output port, the switching unit configured to controllably connect the input port to the second output port in response to a control signal.

The electrosurgical links may connect at least two of the electrosurgical connection units to the electrosurgical channel in a star configuration.

The electrosurgical system may further comprise a second electrosurgical network comprising a plurality of electrosurgical links connecting the input ports of the electrosurgical connection units to a second electrosurgical channel.

The electrosurgical channel and the second electrosurgical channel may be controlled by a same electrosurgical generator.

The electrosurgical channel and the second electrosurgical channel may be controlled by different electrosurgical generators.

At least one of the electrosurgical connection units may further comprise a second output port and the at least one electrosurgical connection unit is configured to connect the electrosurgical channel to the output port and to connect the second electrosurgical channel to the second output port.

One of the first and second electrosurgical channels may be a bipolar electrosurgical channel and the other of the first and second electrosurgical channels may be a monopolar electrosurgical channel.

The first and second electrosurgical channels may be bipolar electrosurgical channels.

The first and second electrosurgical channels may be monopolar electrosurgical channels.

At least one of the electrosurgical connection units may comprise a switching unit situated between the input port and the output port, and the switching unit is configured to controllably connect one of the electrosurgical channel and the second electrosurgical channel to the output port in response to a control signal.

The electrosurgical channel and the second electrosurgical channel may of a same type.

Each link of the electrosurgical network may comprise a plurality of electrosurgical conductors; the electrical output device is an electrosurgical multiplexer; and, the electrosurgical multiplexer is connected to a plurality of electrosurgical channels and is configured to dynamically connect one or more of the plurality of electrosurgical channels to one or more of the electrosurgical conductors in response to a control signal.

Each electrosurgical connection unit may comprise a switching unit between the input port and the output port and the switching unit is configured to controllably connect one or more electrosurgical conductors of the electrosurgical links to the output port in response to a control signal.

At least one of the electrosurgical connection units may comprise a second output port and the switching unit of the at least one electrosurgical connection unit is configured to controllably connect one or more electrosurgical conductors of the electrosurgical links to the second output port in response to the control signal.

At least one of the electrosurgical channels may be a monopolar electrosurgical channel and at least one of the electrosurgical channels may be a bipolar electrosurgical channel.

The first and second electrosurgical channels may be bipolar electrosurgical channels.

The first and second electrosurgical channels may be monopolar electrosurgical channels.

The control unit may be configured to transmit one or more control signals to the electrosurgical connection unit and/or the electrosurgical output device to cause the output port of only one electrosurgical connection unit to be connected to the electrosurgical channel.

The electrosurgical system may further comprise an electrosurgical generator configured to drive the electrosurgical channel.

The control unit may be further configured to detect the location of the electrosurgical generator and transmit the one or more control signals based on the detection.

The electrosurgical system may further comprise a plurality of robot arms, each robot arm comprising: an attachment structure for removably attaching a surgical instrument to the robot arm; and one of the electrosurgical connection units for connecting an electrosurgical instrument attached to the robot arm to an electrosurgical channel.

Each robot arm may comprise a robot arm base connected to a distal robot arm link via a series of intermediate articulated robot arm links.

A second aspect provides an electrosurgical connection unit for a surgical robot arm comprising: an input port configured to receive a driving electrosurgical signal from an electrosurgical output device; an output port configured to output a driving electrosurgical signal to an electrosurgical input device; and a switching unit situated between the input port and the output port, the switching unit configured to controllably connect the input port to the output port in response to a control signal so that a driving electrical signal received on the input port is output on the output port.

The electrosurgical connection unit may further comprise a second output port for outputting the driving electrosurgical signal to another electrosurgical input device.

The other electrosurgical input device may be another electrosurgical connection unit connected to another surgical robot arm.

The electrosurgical connection unit may further comprise a second switching unit configured to controllably connect the input port to the second output port in response to a control signal.

The input port may be configured to receive the driving electrosurgical signal on a first electrosurgical conductor of the input port and a second driving electrosurgical signal on a second electrosurgical conductor of the input port, and the switching unit is configured to controllably connected one of the first and second electrosurgical conductors to the output port in response to a control signal.

The input port may comprise a plurality of electrosurgical conductors and the control unit is configured to controllably connect a subset of the plurality of electrosurgical conductors to the output port in response to a control signal.

The output port may be further configured to receive a return electrosurgical signal, the input port is further configured to output a return electrosurgical signal, and when the switching unit connects the input port to the output port a driving electrosurgical signal received on the input port is output on the output port and a corresponding return electrosurgical signal received on the output port is output on the input port.

The output port may be configured to be connected to an electrosurgical instrument attached to the surgical robot arm.

The input port may be configured to be connected to an electrosurgical network connected to an electrosurgical output device.

A third aspect provides a surgical robot arm comprising the electrosurgical connection unit of the second aspect.

A fourth aspect provides an electrosurgical system comprising: a plurality of electrosurgical connection units, each electrosurgical connection unit comprising an input port connectable to an electrosurgical channel and an output port connectable to an electrosurgical instrument, the electrosurgical connection unit configured to connect the input port to the output port; an electrosurgical network comprising a plurality of electrosurgical links that connect the input ports of the electrosurgical connection units to an electrosurgical channel; and a control unit configured to: receive information from a device indicating that the device has detected an electrosurgical generator connected to the electrosurgical channel, the device being one of the electrosurgical connection units and an electrosurgical output device connected to the electrosurgical channel; determine a location of the electrosurgical generator in the electrosurgical network based on the received information; and transmit one or more control signals to the electrosurgical connection units and/or one or more electrosurgical output devices connected to the electrosurgical channel to cause the output port of a selected combination of electrosurgical connection units to be connected to the electrosurgical channel based on the determined location of the electrosurgical generator.

Each electrosurgical connection unit may comprise an electrosurgical generator cable detection unit configured to detect when an electrosurgical generator cable has been inserted in the electrosurgical connection unit, and in response to detecting that an electrosurgical generator cable has been inserted in the electrosurgical connection unit notify the control unit of the detection.

The electrosurgical generator cable detection unit may comprise at least one of a mechanical sensor, an electrical sensor, an optical sensor and a magnetic sensor configured to detect when an electrosurgical generator cable has been inserted in the electrosurgical connection unit.

Each of the electrosurgical connection units is configured to notify the control unit of a detection by, modifying a message received from the control unit to indicate the detection and transmitting the modified message to the control unit.

The input port of each electrosurgical connection unit may comprise a driving electrosurgical signal detection unit configured to, when operating in a test mode, detect when a driving electrosurgical signal is received on the input port, and in response to detecting that a driving electrosurgical signal has been detected on the input port notify the control unit of the detection.

The electrosurgical generator may be configured to detect when the electrosurgical generator is connected to the electrosurgical channel and in response to detecting that the electrosurgical generator is connected to the electrosurgical channel notify the control unit of the detection along with information indicating the location of the electrosurgical generator in the electrosurgical network.

Each electrosurgical connection unit may further comprise a switching unit situated between the input port and the output port, the switching unit configured to controllably connect the input port to the output port in response to a control signal.

The one or more control signals transmitted by the control unit may cause a selected combination of electrosurgical links to be active and all other electrosurgical links to be inactive.

The electrosurgical system may further comprise a second electrosurgical network comprising a plurality of electrosurgical links connecting the input ports of the electrosurgical connection units to a second electrosurgical channel.

The electrosurgical channel and the second electrosurgical channel are driven by a same electrosurgical generator; or the electrosurgical channel and the second electrosurgical channel are driven by different electrosurgical generators.

At least one of the electrosurgical connection units may further comprise a second output port and the at least one electrosurgical connection unit is configured to connect the electrosurgical channel to the output port and to connect the second electrosurgical channel to the second output port.

At least one of the electrosurgical connection units may comprise a switching unit situated between the input port and the output port, and the switching unit is configured to dynamically connect the electrosurgical channel to the output port in response to a first control signal and dynamically connect the second electrosurgical channel to the output port in response to a second, different, control signal.

The electrosurgical channel and the second electrosurgical channel may be of a same type.

Each electrosurgical link of the electrosurgical network may comprises a plurality of electrosurgical conductors; and the system further comprises an electrosurgical multiplexer configured to receive the first electrosurgical channel and a second electrosurgical channel and dynamically connect one or more of the electrosurgical channel and the second electrosurgical channels to one or more of the electrosurgical conductors in response to a control signal.

Each electrosurgical connection unit may comprise a switching unit situated between the input port and the output port, the switching unit configured to controllably connect one or more electrosurgical conductors of the electrosurgical links to the output port in response to a control signal.

At least one of the electrosurgical connection units may comprise a second output port and the switching unit of the at least one electrosurgical connection unit is configured to controllably connect one or more electrosurgical conductors of the electrosurgical links to the second output port in response to a control signal.

One of the electrosurgical channel and the second electrosurgical channel may a bipolar electrosurgical channel and the other of the electrosurgical channel and the second electrosurgical channel is a monopolar electrosurgical channel.

The electrosurgical channel and the second electrosurgical channel may both be bipolar electrosurgical channels; or the electrosurgical channel and the second electrosurgical channel may both be monopolar electrosurgical channels.

The control unit may be configured to transmit one or more control signals to the electrosurgical connection units and/or the electrosurgical output device to cause the output port of only one electrosurgical connection unit to be connected to the electrosurgical channel.

The electrosurgical system may further comprise a plurality of robot arms, each robot arm comprising: an attachment structure for removably attaching a surgical instrument to the robot arm; and one of the electrosurgical connection units for connecting an electrosurgical instrument attached to the robot arm to the electrosurgical channel.

The above features may be combined as appropriate, as would be apparent to a skilled person, and may be combined with any of the aspects of the examples described herein.

BRIEF DESCRIPTION OF THE DRAWINGS

Examples will now be described in detail with reference to the accompanying drawings in which.

Figure 1:
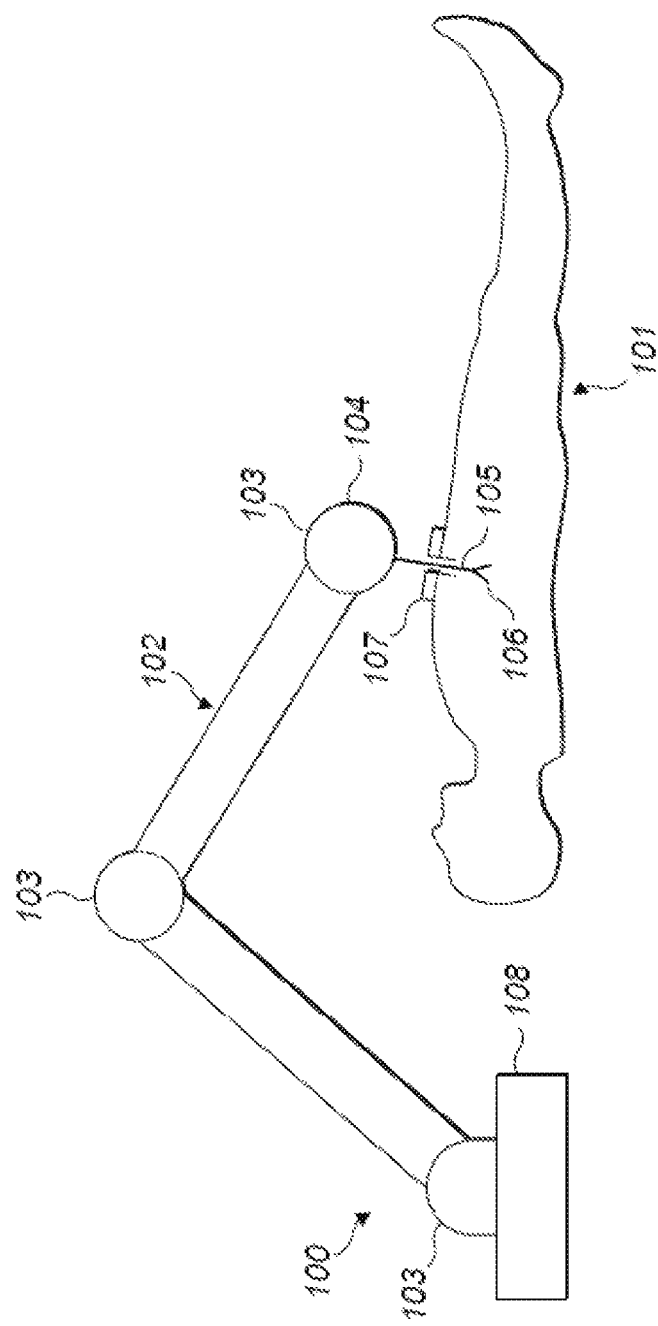
FIG. 1 is a schematic diagram of an example surgical robot performing a surgical procedure.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Described herein are electrosurgical systems that comprise an electrosurgical network that connects a plurality of electrosurgical connection units (to which an electrosurgical instrument can be attached) to one or more electrosurgical channels such that any of the one or more electrosurgical channels can be provided to any combination of electrosurgical connection units. Where the electrosurgical connection units are in physically separate locations of an operating room (e.g. one electrosurgical connection unit may be situated on a left side of a patient bed, and another electrosurgical connection unit may be situated on a right side of a patent bed) such electrosurgical systems allow an electrosurgical instrument to be located in a variety of locations throughout the operating room yet controlled/driven by any of the electrosurgical channels. This allows electrosurgical instruments to be easily placed in different locations for different surgical procedures, yet controlled by the same electrosurgical channel. Such electrosurgical systems also reduce reconfiguration errors that may be caused in systems where an electrosurgical instrument needs to be moved during a surgical procedure to a different location in the operating room on the fly.

Example electrosurgical systems will be described below in the context of a surgical robot system where an electrosurgical instrument is connected to a surgical robot arm which controls the location and movement of that electrosurgical instrument. In these examples, the electrosurgical connection units are each connected to one of a plurality of robot arms and are configured to dynamically connect a surgical instrument attached to the robot arm to one of one or more electrosurgical channels. However, it will be evident to a person of skill in the art that the electrosurgical systems described herein may also be used in a non-robotic surgical context. For example, instead of the electrosurgical connection units being connected to a robot arm the electrosurgical connection units may be placed in various locations around an operating room (e.g. they may be connected to opposing sides of a patient bed) and may be used to dynamically connect a manually controlled electrosurgical instrument to one of one or more electrosurgical channels.

Figure 4:
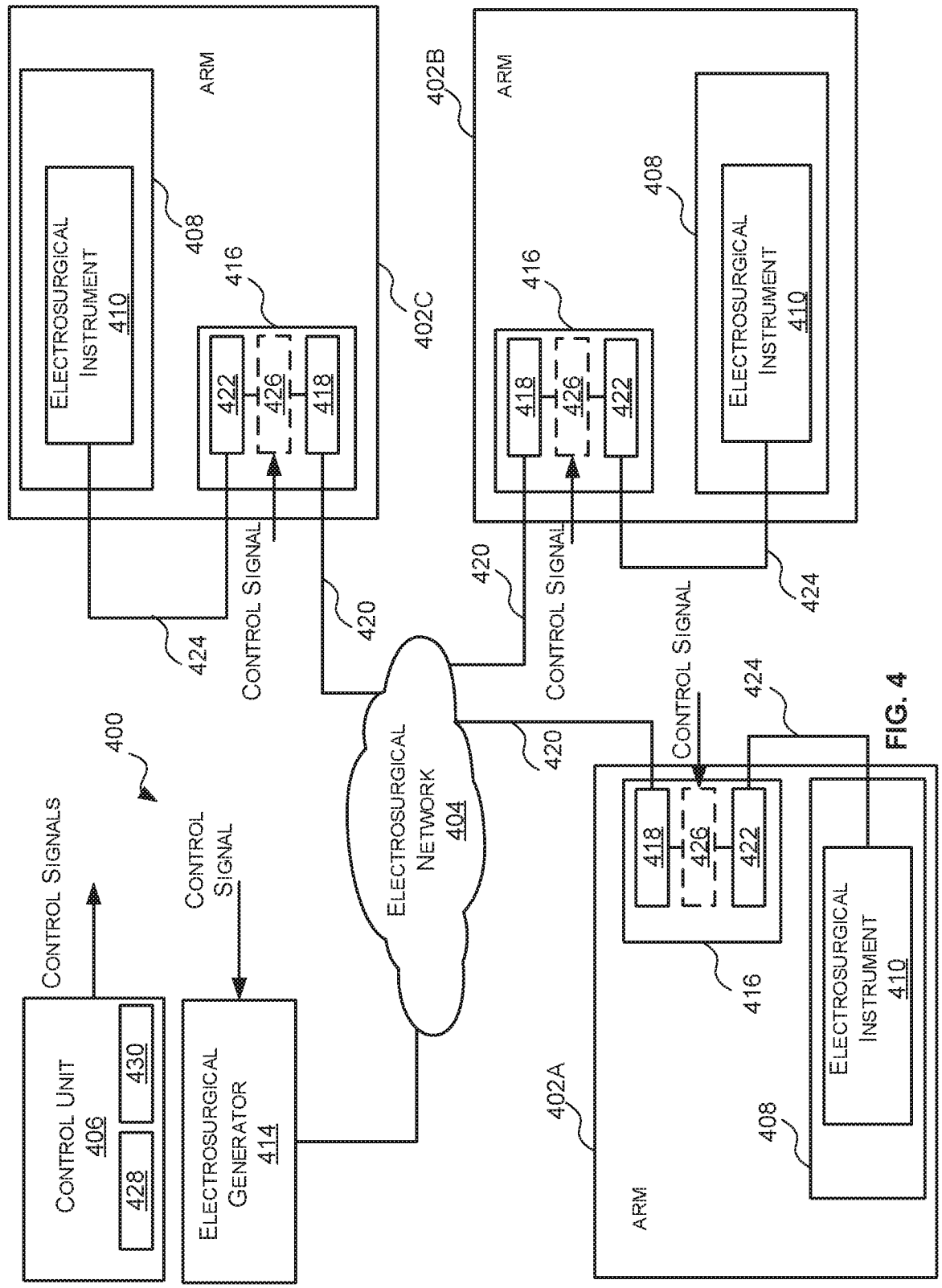
FIG. 4 is a schematic diagram of an example electrosurgical system in which a plurality of robot arms are connected to an electrosurgical channel controlled by an electrosurgical generator.

Reference is now made to FIG. 4 which shows a first example electrosurgical system 400 in which an electrosurgical network 404 connects a plurality of electrosurgical connection units 416 (which can be connected an electrosurgical instrument) to an electrosurgical channel controlled by an electrosurgical generator 414. In this example, the surgical instruments, are robotically controlled by a robot arm 402A, 402B, 402C and thus each electrosurgical connection unit 416 is connected to a robot arm 402A, 402B, 402C and is configured to connect an electrosurgical instrument connected to that arm to the electrosurgical channel.

The system 400 of FIG. 4 comprises three robot arms 402A, 402B, 402C. However, it will be evident to a person of skill in the art that the methods and principles may be applied to any robotic surgical system with two or more robot arms. Each robot arm 402A, 402B, 402C comprises an attachment structure 408 at its distal end for removably attaching a surgical instrument to the arm. At its distal end, the instrument 410 comprises an end effector for engaging in a medical procedure. An example implementation of a robot arm 402 is described below with respect to FIG. 5.

A variety of instrument types are known, each adapted to perform a particular surgical function. Each arm 402 may be capable of receiving any type of instrument. An example type of instrument is an electrosurgical instrument 410 which is adapted to perform an electrosurgical function. As described above, electrosurgery is the passing of a high frequency (i.e. radio frequency) current through tissue to cause a desired effect (e.g. cutting the tissue or coagulating the tissue). There are two types of electrosurgery—monopolar and bipolar. In monopolar electrosurgery the high frequency current passes through the patient from a live or active electrode on the electrosurgical instrument to a separate return electrode (not shown) placed on the patient, which may also be referred to as an indifferent electrode or a patient electrode. In bipolar electrosurgery the active and return electrodes are combined within the electrosurgical instrument and the current passes through the patient from the active electrode on the electrosurgical instrument to the return electrode on the electrosurgical instrument. An electrosurgical instrument which is configured for monopolar electrosurgery (e.g. an electrosurgical instrument that comprises an active electrode only) will be referred to herein as a monopolar electrosurgical instrument, and an electrosurgical instrument which is configured for bipolar electrosurgery (e.g. an electrosurgical instrument that comprises both an active electrode and a return electrode) will be referred to herein as a bipolar electrosurgical instrument.

Electrosurgical instruments receive the driving current (which may be referred to as a driving electrosurgical signal) from an electrosurgical generator 414 which may also be referred to as an electrosurgery generator, electrosurgical end unit, electrosurgery end unit, or ESU. Electrosurgical generators can typically be configured to generate multiple different current waveforms to achieve different surgical effects. For example, many standard electrosurgical generators can be configured to generate COAG, CUT and BLEND waveforms. The COAG waveform consists of bursts of radio frequency, which when used at a low power setting causes a desiccation effect, and when used at a high-power setting causes a fulguration effect. The CUT waveform is a continuous waveform at lower voltage, but higher current than COAG, which causes the tissue to be cut. The BLEND waveform is between a CUT waveform and a COAG waveform, but is not a combination thereof. A BLEND waveform is essentially a CUT waveform with a lower duty cycle than a CUT waveform. A BLEND waveform typically has a duty cycle between 15% to 75%. The off time allows the tissue to cool creating some haemostasis. Accordingly, a BLEND waveform is used where haemostasis is required as tissue is cut. It will be evident to a person of skill in the art that these are examples only and that different electrosurgical generators may be configured to generate different and/or additional waveforms.

An electrosurgical generator 414 may comprise any suitable means for configuring the waveform(s) to be produced. For example, an electrosurgical generator 414 may comprise mechanical means, such as switches, buttons, dials etc., for configuring the waveform(s) to be produced. Alternatively, or in addition, an electrosurgical generator 414 may be configured electronically, such as via a control signal transmitted to the electrosurgical generator 414. For example, the electrosurgical generator may be connected to the robot control system used to control the robot arms 402A, 402B, 402C (described in more detail below) and from the command interface of the robot control system the surgeon, or other user, may be able to configure the waveform(s) to be produced. The robot control system may then transmit the configuration of the waveform(s) to the electrosurgical generator 414 which causes the electrosurgical generator 414 to configure itself so that it can generate a current with the configured waveform(s).

There is also typically means for causing a current having a configured waveform (which may be referred to herein as a driving electrosurgical signal) to be applied to an active electrode of an electrosurgical instrument connected to the electrosurgical generator. In some cases, the electrosurgical generator 414 may be configured to output a driving electrosurgical signal in response to receiving an activation signal. In these cases, the electrosurgical generator 414 may comprise, or be connected, to a manual trigger mechanism such as, but not limited to, a pedal or button which, when activated by a user, causes the electrosurgical generator 414 to output a driving electrosurgical signal (e.g. current with a configured waveform). In other cases, the electrosurgical generator 414 may be connected to the robot control system and from the command interface thereof the surgeon, or other user, may be able to indicate that the electrosurgical generator 414 is to output a driving electrosurgical signal. That indication may then be directly transmitted to the electrosurgical generator 414 as an activation signal which causes the electrosurgical generator 414 to output a driving electrosurgical signal (i.e. current with the selected/configured waveform); or the indication may be transmitted to the electrosurgical connection unit described below, as a control signal, which causes the electrosurgical connection unit to transmit an activation signal to the electrosurgical generator.

In other cases, however, the electrosurgical generator 414 may be configured to output a driving electrosurgical signal as soon as it is powered on and the electrosurgical generator 414 and the active electrode of the electrosurgical instrument may be controllably connected in response to input from the user. For example, where the electrosurgical instrument is manually controlled (as opposed to robotically controlled) the electrosurgical instrument may have a manual trigger mechanism, such as a button, which when activated by the user causes the driving electrosurgical signal output by the electrosurgical generator to be provided to the active electrode of the electrosurgical instrument. Where the electrosurgical instrument is robotically controlled, such as in the example of FIG. 4, the electrosurgical connection unit 416 may be configured to dynamically provide the driving electrosurgical signal output by the electrosurgical generator to the active electrode of the electrosurgical instrument in response to a control signal generated in response to a trigger input received from the user. This will be described in more detail below.

Each robot arm 402A, 402B, 402C also comprises an electrosurgical connection unit 416 which is configured to act as electrosurgical interface between the electrosurgical network 404 and an electrosurgical instrument attached to the robot arm 402A, 402B, 402C. Specifically, the electrosurgical connection unit 416 is configured to receive a driving electrosurgical signal from the electrosurgical network 404 and output the received driving electrosurgical signal to an electrosurgical instrument attached to the robot arm 402A, 402B, 402C. In some cases, the electrosurgical connection unit 416 may also be configured to receive a return electrosurgical signal from an electrosurgical instrument attached to the robot arm 402A, 402B or 402C, or a patient electrode connected to the electrosurgical connection unit, and output the received return electrosurgical signal to the electrosurgical network 404.

In some examples, the electrosurgical connection unit 416 may comprise an input port 418 connectable to the electrosurgical network 404; and an output port 422 connectable to an electrosurgical instrument attached to the arm. The electrosurgical connection unit 416 is configured to receive a driving electrosurgical signal on the input port 418 and output the driving electrosurgical signal on the output port 422. In some cases, the input port 418 may be configured to receive one or more electrosurgical cables 420 connected to (directly or indirectly), or forming part of, the electrosurgical network 404. In other cases the input port may be integrated with a cable which can be connected to the electrosurgical network 404. Similarly, the output port 422 may be configured to receive one or more electrosurgical cables 424 connected to (directly or indirectly) to the electrosurgical instrument. In other cases, the output port may be integrated with a cable with can be connected (directly or indirectly) to the electrosurgical instrument.

In some cases, the input port 418 and the output port 422 may be permanently connected (via, for example, a wire or conductor, or set of wires or conductors) such that any driving electrosurgical signal received via the input port 418 is automatically output on the output port 422, and, similarly any return electrosurgical signal received via the output port 422 is automatically output on the input port 418. In other cases, the electrosurgical connection units 416 may further comprise a switching unit 426 situated between the input port 418 and the output port 422 that is configured to controllably connect the input port 418 to the output port 422 in response to a control signal received from the electrosurgical control unit 406. In some cases, the switching unit 426 comprises one or more switches in series with the input port 418 and the output port 422. In these cases, the input port 418 is dynamically connected to the output port 422 by closing the switches of the switching unit 426. The switches may be implemented by relays such as electromechanical relays (EMR) or steady-state relays (SSR).

An electrosurgical connection unit 416 may receive the control signals from the electrosurgical control unit 406 via any suitable communication means. For example, the electrosurgical control unit 406 may be able to establish a wireless communication link with an electrosurgical connection unit 416 and transmit the control signal over the wireless communication link. In other examples, the electrosurgical control unit 406 may be connected to an electrosurgical connection unit 416 via a wired communications link.

The electrosurgical network 404, which may also be referred to herein as an electrosurgery network, an ES-network or ESN, comprises a plurality of electrosurgical links which connect the plurality of electrosurgical connection units to an electrosurgical channel controlled by an electrosurgical generator. An electrosurgical channel is a set of wires that are used to transport a set of signals that are transported to or from an electrosurgical instrument to control the operation of the electrosurgical instrument. The number of signals, that an electrosurgical channel carries is based on the type of electrosurgical channel. For example, a bipolar electrosurgical channel carries at least a driving electrosurgical signal and the return electrosurgical signal. In contrast, a monopolar electrosurgical channel carries at least a driving electrosurgical signal.

An electrosurgical channel is controlled by an electrosurgical generator 414. Specifically, the electrosurgical generator 414 generates the driving electrosurgical signal of the electrosurgical channel. The electrosurgical network 404 may be directly connected to the electrosurgical generator 414 which controls the electrosurgical channel or may be indirectly connected to the electrosurgical generator 414 which control the electrosurgical channel. In the example of FIG. 4 the electrosurgical network 404 is directly connected to the electrosurgical generator 414, but in other examples the electrosurgical network 404 may be connected to another electrosurgical output device (a device that is capable of outputting a driving electrosurgical signal) such as an electrosurgical distribution unit or an electrosurgical multiplexer (which are described in more detail below).

An electrosurgical link is a set of one or more electrosurgical wires (which also may be referred to an electrosurgical bus, an electrosurgical rail or an electrosurgical conductor) to carry the electrosurgical signals of an electrosurgical channel. The number of wires forming each electrosurgical link depends on the type of electrosurgical channel supported by the electrosurgical network 404. For example, where the electrosurgical network 404 is designed to support a bipolar electrosurgical channel each electrosurgical link comprises at least two wires—one wire to carry the driving electrosurgical signal to the electrosurgical instrument(s) to be controlled thereby, and a second wire to carry the return electrosurgical signal captured by the return electrode. Accordingly, in these examples both the generated signal and the return signal are transported through the electrosurgical network 404.

Some electrosurgical generators are configured to generate a driving electrosurgical signal for a bipolar electrosurgical instrument in response to receiving a bipolar activation signal. In some cases the bipolar activation signal may be generated by the electrosurgical connection unit. In these cases, the electrosurgical links may comprise an additional wire to transport the bipolar activation signal through the electrosurgical network 404. In other cases, the bipolar activation signal may be generated by another device. In these cases, the electrosurgical links may not comprise a wire to transport the bipolar activation signal through the electrosurgical network 404.

In another example, where the electrosurgical network 404 is configured to support a monopolar electrosurgical channel each electrosurgical link may comprise at least one wire to carry the electrosurgical signal generated by the electrosurgical generator 414 to the electrosurgical instrument. In some cases, the patient electrode may be connected to the electrosurgical generator 414 via a separate connection and the return electrosurgical signal is provided to the electrosurgical generator via this separate connection. In these cases, the electrosurgical links may not include an additional wire to transport the return electrosurgical signal through the electrosurgical network. In other cases, the patient electrode may be connected to the electrosurgical connection unit and the return electrosurgical signal captured by the patient electrode may be transmitted to the electrosurgical generator by the electrosurgical network 404. In these cases, the electrosurgical links may comprise an additional wire to transport the return electrosurgical signal through the electrosurgical network.

Some electrosurgical generators that can generate both CUT and COAG driving electrosurgical signals for a monopolar electrosurgical instrument are configured to generate and output a CUT driving electrosurgical signal in response to receiving a CUT activation signal, and output a COAG driving electrosurgical signal in response to receiving a COAG driving electrosurgical signal. In some cases, the electrosurgical connection units may be configured to generate the CUT and COAG activation signals. In these cases, the electrosurgical links may comprise two additional wires to transport the CUT and COAG activation signals through the electrosurgical network 404. In other cases, however, the CUT and COAG activation signals may be generated by another device. In these cases, the electrosurgical links may not comprise wires for transporting the CUT and COAG activation signals through the electrosurgical network. This allows the cables of the electrosurgical links to be smaller and lighter.

In some examples, the electrosurgical network 404 may be configured so that the electrosurgical connection units 416 of the arms 402A, 402B, 402C are connected in a star-configuration. In a star-configuration each electrosurgical connection unit 416 receives the driving electrosurgical signal generated by the electrosurgical generator 414 via a separate or dedicated electrosurgical link. Each dedicated link may directly connect the associated electrosurgical connection unit 416 to the electrosurgical generator 414 or may connect the associated electrosurgical connection unit 416 to an intermediary unit which receives the driving electrosurgical signal from the electrosurgical generator, or another device, and redistributes the signal to the electrosurgical connection unit via the link. Example star configurations for the electrosurgical network 404 are described below with reference to FIGS. 6-8.

In other examples, the electrosurgical network 404 may be configured so that the electrosurgical connection units 416 of the arms 402A, 402B, 402C are connected in a daisy-chain configuration. In a daisy-chain configuration the electrosurgical connection units 416 of the plurality of arms 402A, 402B, 402C are connected to each other in a serial sequence. For example, the electrosurgical connection unit 416 of the first arm 402A may be connected via an electrosurgical link to the electrosurgical connection unit 416 of the second arm 402B, and the electrosurgical connection unit 416 of the second arm 402B may then be connected to the electrosurgical connection unit 416 of the third arm 402C via another electrosurgical link. The driving electrosurgical signal generated by the electrosurgical generator 414 can be provided to any of the electrosurgical connection units 416 and redistributed to the other electrosurgical connection units 416 via the chain.

Where the electrosurgical network 404 is configured so that the electrosurgical connection units 416 are daisy-chained, one or more of the electrosurgical connection units 416 may comprise one or more additional output ports so as to be able to provide a received driving electrosurgical signal to another electrosurgical connection unit 416 in the chain. In some cases, the input port may be permanently connected, or hardwired, to the additional output port(s) such that any driving electrosurgical signal received on the input port is automatically output on the additional output port(s). In other cases, the electrosurgical connection units 416 may comprise one or more switching units that are situated between the input port and the additional output port(s) and the switching unit(s) are configured to controllably connect the input port and the additional output port(s) based on a control signal. This will be described in more detail below. Example daisy chain configurations for the electrosurgical network 404 are described below with reference to FIGS. 9-11.

It will be evident to a person of skill in the art that these are example configurations for the electrosurgical network 404 only and that electrosurgical network 404 may connect the electrosurgical connection units 416 to the electrosurgical generator 414 in any suitable manner. For example, the electrosurgical network 404 may alternatively connect the electrosurgical connection units 416 to the electrosurgical generator 414 using a combination of a star configuration and a daisy chain configuration. Specifically, two or more of the electrosurgical connection units 416 may be daisy-chained together such that at least one of electrosurgical connection units 416 is connected to the electrosurgical generator 414 via another electrosurgical connection unit 416, and one or more other electrosurgical connection units 416 may be connected to the electrosurgical generator via a star configuration.

The electrosurgical control unit 406 is a device that is connected to the electrosurgical output device (e.g. electrosurgical generator 414) and/or the electrosurgical connection units 416 to control the operation of the electrosurgical output device (e.g. electrosurgical generator 414) and/or the electrosurgical connection units 416 to cause an electrosurgical connection to be established between the electrosurgical output device (e.g. electrosurgical generator 414) and the output port 422 of a selected combination of electrosurgical connection units 416. The combination of electrosurgical connection units 416 may be selected based on a number of criteria, such as, but not limited to which robot arms 402A, 402B, 402C have an electrosurgical instrument 410 attached thereto, and which electrosurgical instruments are to be controlled or energised.

In some cases, the electrosurgical control unit 406 may be configured to selectively enable and disable links of the electrosurgical network 404 so that only selected electrosurgical connection units 416 receive a driving electrosurgical signal generated by the electrosurgical generator 414. Where the electrosurgical connection units 416 are connected in a star configuration the electrosurgical control unit 406 may be configured to transmit a control signal to an electrosurgical distribution device to which the electrosurgical connection units 416 are connected to cause the electrosurgical distribution device to only output a driving electrosurgical signal received/generated by the electrosurgical generator 414 over a selected set of links. In these cases, the electrosurgical connection units 416 may only receive a driving electrosurgical signal when the driving electrosurgical signal is to control the operation of an electrosurgical instrument attached thereto. Where, however, the electrosurgical connection units 416 are connected in a daisy-chain configuration, the electrosurgical control unit 406 may be configured to transmit control signals to the electrosurgical connection units 416 which causes the electrosurgical connection units 416 to enable or disable selected links in the chain so that the electrosurgical signal is only provided to a selected set of electrosurgical connection units 416.

In other cases, where the electrosurgical connection units 416 comprise a switching unit situated between the input port 418 and the output port 422, the electrosurgical control unit 406 may be configured to enable the connection between the input port 418 and output port 422 of selected electrosurgical connection units 416 by transmitting control signals to the electrosurgical connection units 416.

In yet other cases, the electrosurgical control unit 406 may be configured to both selectively enable and disable links of the electrosurgical network 404 and selectively enable the connection between the input port 418 and the output port 422 of selected electrosurgical connection units 416.

In some cases, the electrosurgical control unit 406 may be configured to transmit control signals to the electrosurgical connection units 416 and/or the electrosurgical output device to cause the output port of only one electrosurgical connection unit 416 to be connected to the same live electrosurgical channel at any one time. It may be possible, however, to have the output ports of different electrosurgical connection units 416 to be connected to different electrosurgical channels so that different electrosurgical instruments may be simultaneously controlled by different electrosurgical channels.

In some cases, the electrosurgical control unit 406 may receive information that indicates a type of electrosurgical instrument attached to each robot arm 402A, 402B and 402C and the electrosurgical control unit 406 may be configured to use this information to ensure that any electrosurgical instrument is only controlled by an electrosurgical channel that is compatible with that type of electrosurgical instrument. For example, the robot arms 402A, 402B, 402B may be equipped with an RFID reader, or the like, that is able to receive information from a surgical instrument attached to the robot arm 402A, 402B, 402C indicating the type of surgical instrument. This information may be then communicated to the electrosurgical control unit 406 where the electrosurgical control unit 406 ensures that the electrosurgical instrument is only controlled by (or connected to) an electrosurgical channel that is compatible with that type of electrosurgical instrument.

The electrosurgical control unit 406 may comprise one or more processors 428 and a memory 430 that is configured to store computer-executable instructions that when executed by the one or more processors cause the one or more processors to perform the functions described above. In some cases, the electrosurgical control unit 406 may be attached to the command interface (described below) so that the operation of the electrosurgical control unit 406 can be controlled based on input from the surgeon, or other user.

Figure 5:
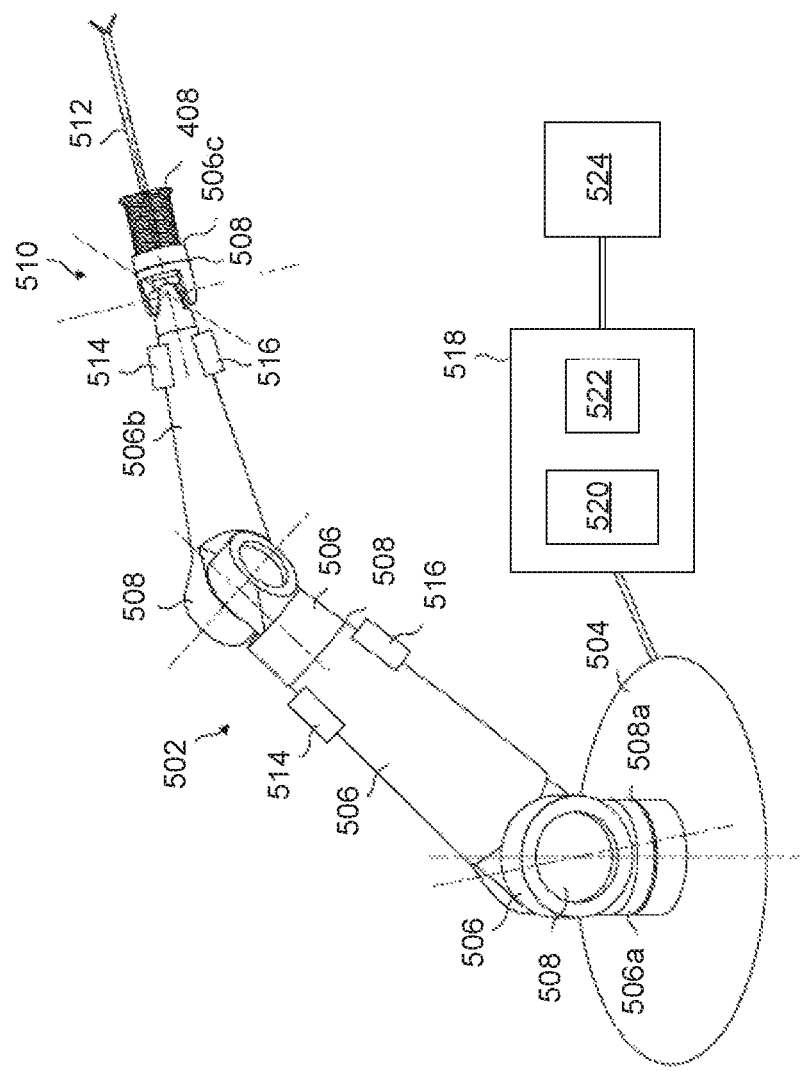
FIG. 5 is a schematic diagram of an example robot arm of FIG. 4.

Reference is now made to FIG. 5 which illustrates an example robot arm 502 which may be used to implement any of the robot arms 402A, 402B and/or 402C of FIG. 4. The robot arm 502 extends from a proximal end attached to a base 504. The arm comprises a number of rigid links 506. The links are coupled by revolute joints 508. The most proximal link 506a is coupled to the base by joint 508a. It and the other links are coupled in series by further ones of the joints 508. Suitably, a wrist 510 is made up of four individual revolute joints. The wrist 510 couples one link (506b) to the most distal link (506c) of the arm. The most distal link 506c is at the distal end of the arm and carries the attachment structure 408 for a surgical instrument 512. Each joint 508 of the arm has one or more motors 514 which can be operated to cause rotational motion at the respective joint, and one or more position and/or torque sensors 516 which provide information regarding the current configuration and/or load at that joint. The motors may be arranged proximally of the joints whose motion they drive, so as to improve weight distribution. For clarity, only some of the motors and sensors are shown in FIG. 5. The arm may be generally as described in our co-pending patent application PCT/GB2014/053523.

Figure 2:
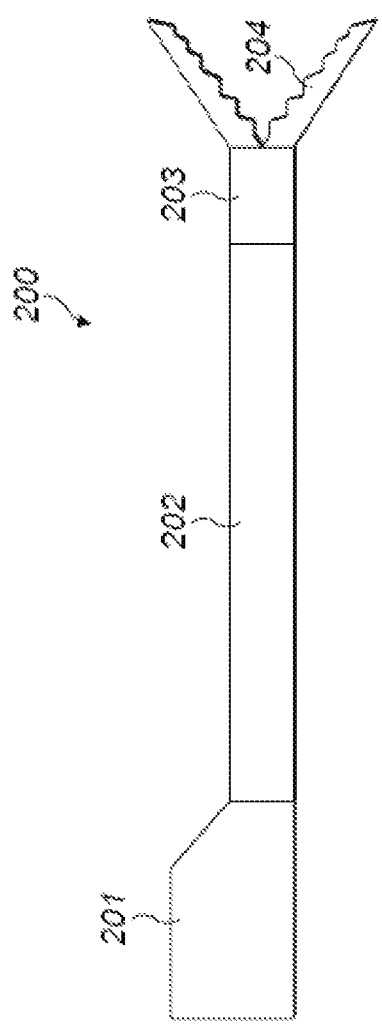
FIG. 2 is a schematic diagram of an example surgical instrument.
Figure 3:
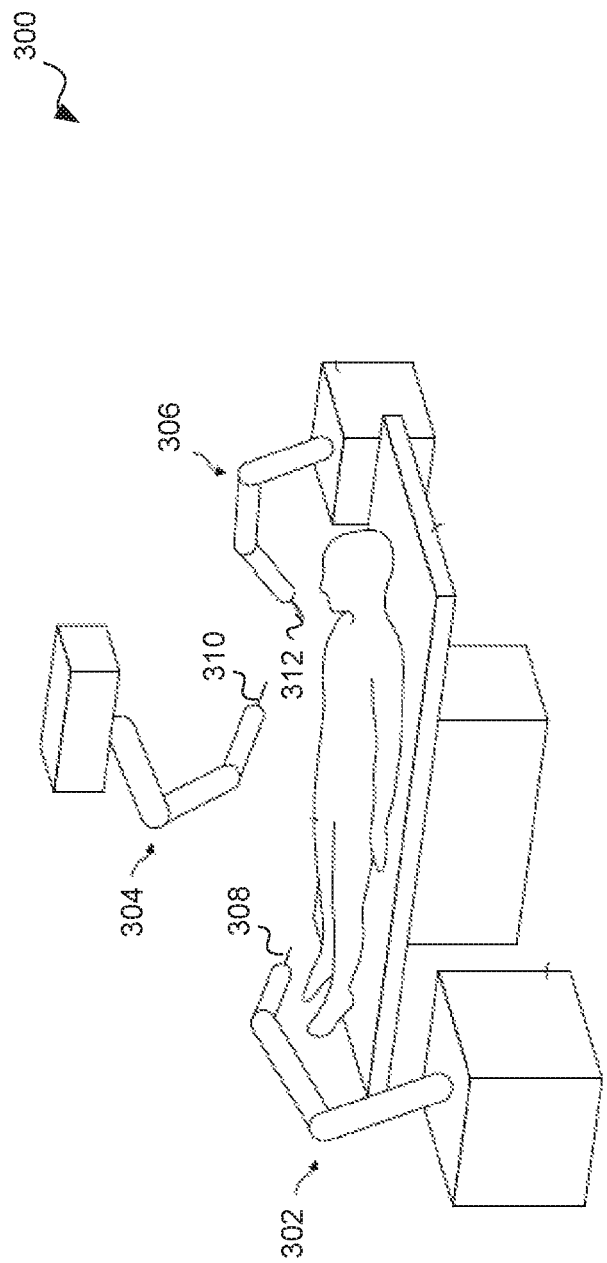
FIG. 3 is a schematic diagram of an example surgical robot system with a plurality of robot arms.

The arm terminates in an attachment structure 408 for interfacing with the instrument 512. The instrument 512 may take the form described with respect to FIG. 2. The attachment structure 408 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 512 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2 the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to a robot control unit 518. The robot control unit 518 comprises a processor 520 and a memory 522. Memory 522 stores in a non-transient way software that is executable by the processor 520 to control the operation of the motors 514 to cause the arm 502 to operate in the manner described herein. In particular, the software can control the processor 520 to cause the motors (for example via distributed controllers) to drive in dependence on inputs from the sensors 516 and from a surgeon command interface 524. The robot control unit 518 is coupled to the motors 514 for driving them in accordance with outputs generated by execution of the software. The robot control unit 518 is coupled to the sensors 516 for receiving sensed input from the sensors, and to the command interface 524 for receiving input from it. The respective couplings may, for example, each be electrical or optical cables, or may be provided by a wireless connection. The command interface 524 comprises one or more input devices whereby a user can request motion of the end effector in a desired way. The input devices could, for example, be manually operable mechanical input devices such as control handles or joysticks, or contactless input devices such as optical gesture sensors. The software stored in memory 522 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 524 can control the instrument 512 to move in such a way as to perform a desired surgical procedure. The robot control unit 518 and/or the command interface 524 may be remote from the arm 502.

Where there are multiple arms, each arm may be controlled by the same robot control unit 518 or by a different robot control unit 518.

Figure 6:
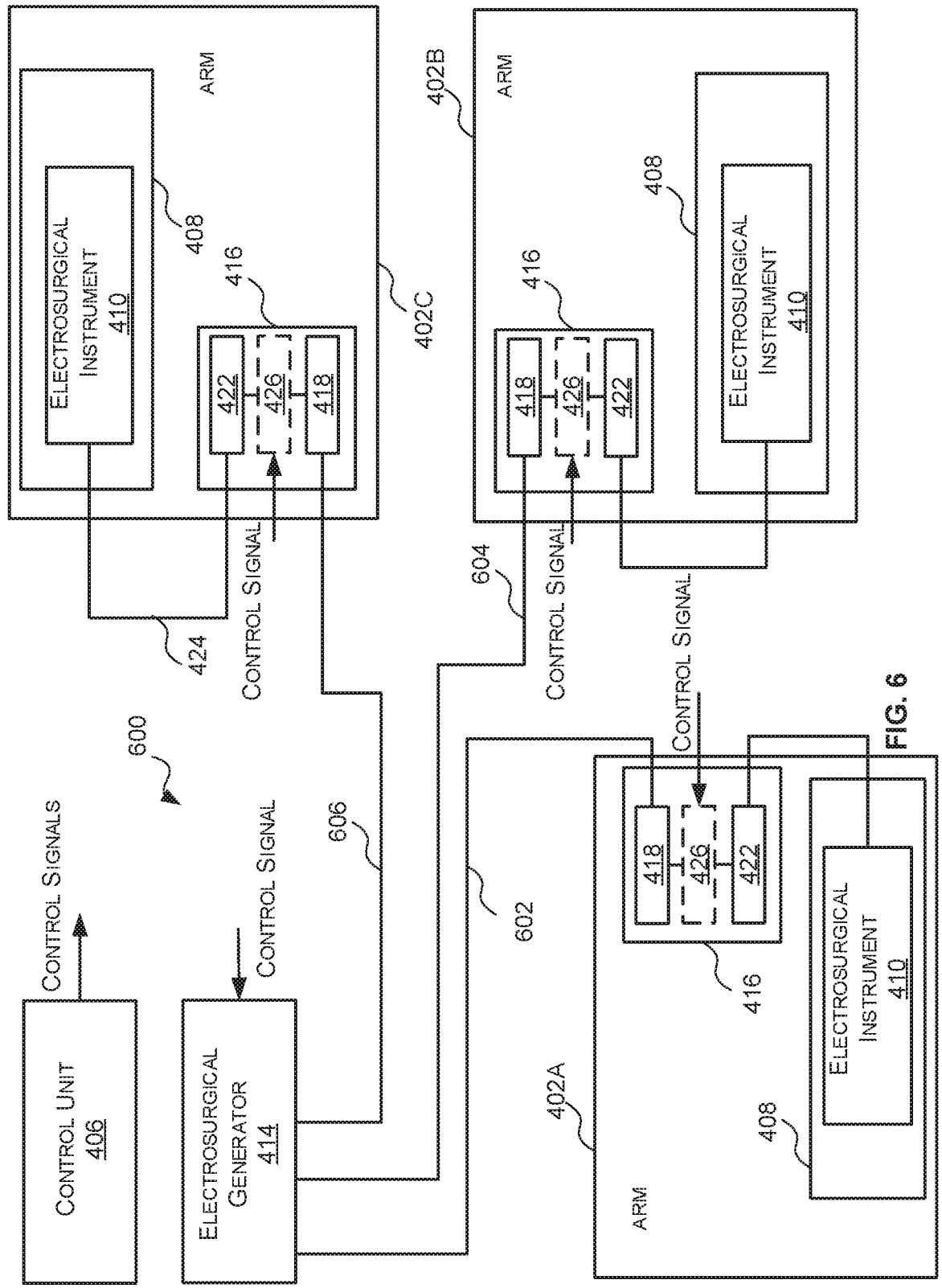
FIG. 6 is a schematic diagram of the electrosurgical system of FIG. 4 where the electrosurgical network has a first example star configuration.
Figure 7:
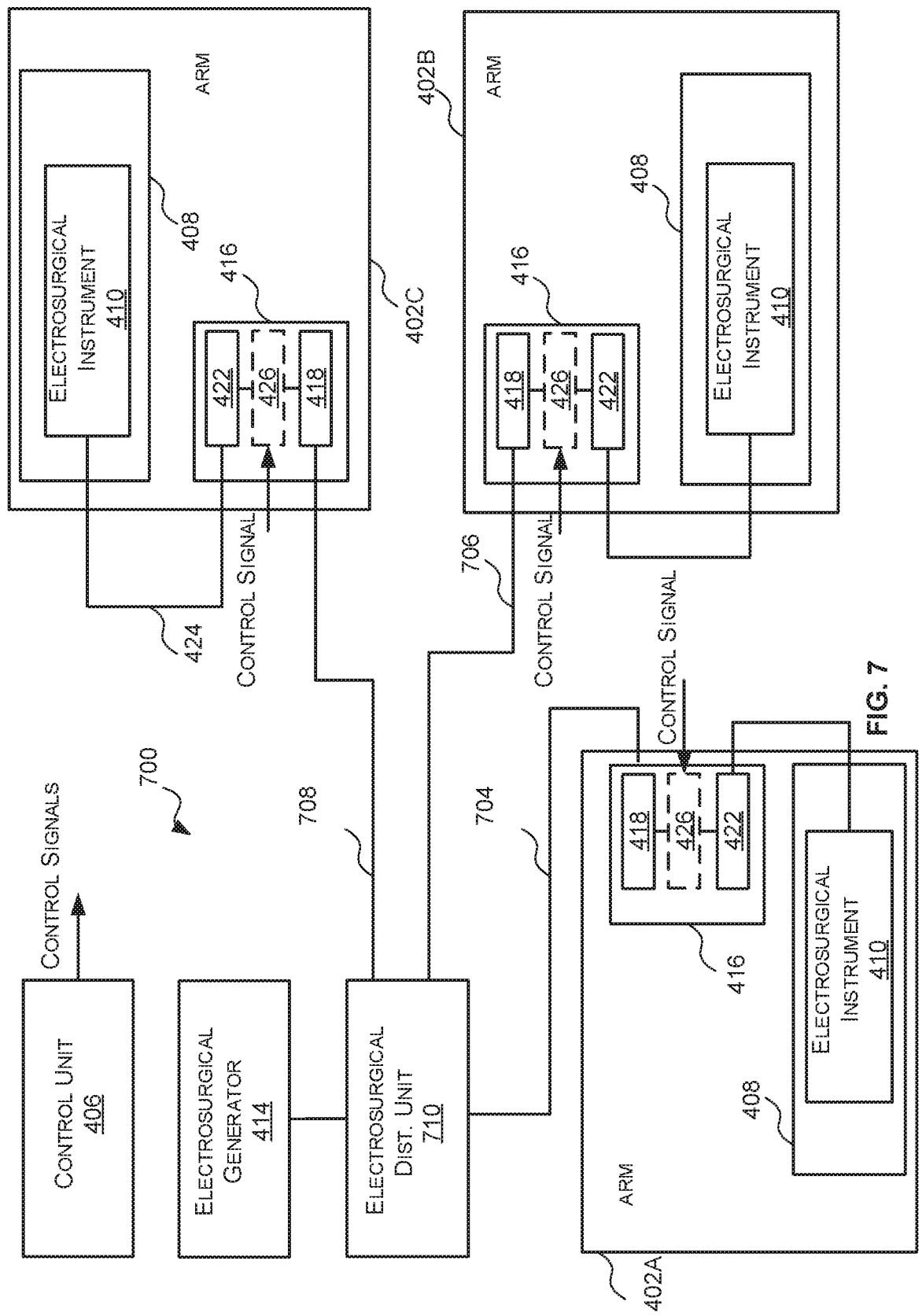
FIG. 7 is a schematic diagram of the electrosurgical system of FIG. 4 where the electrosurgical network has a second example star configuration.
Figure 8:
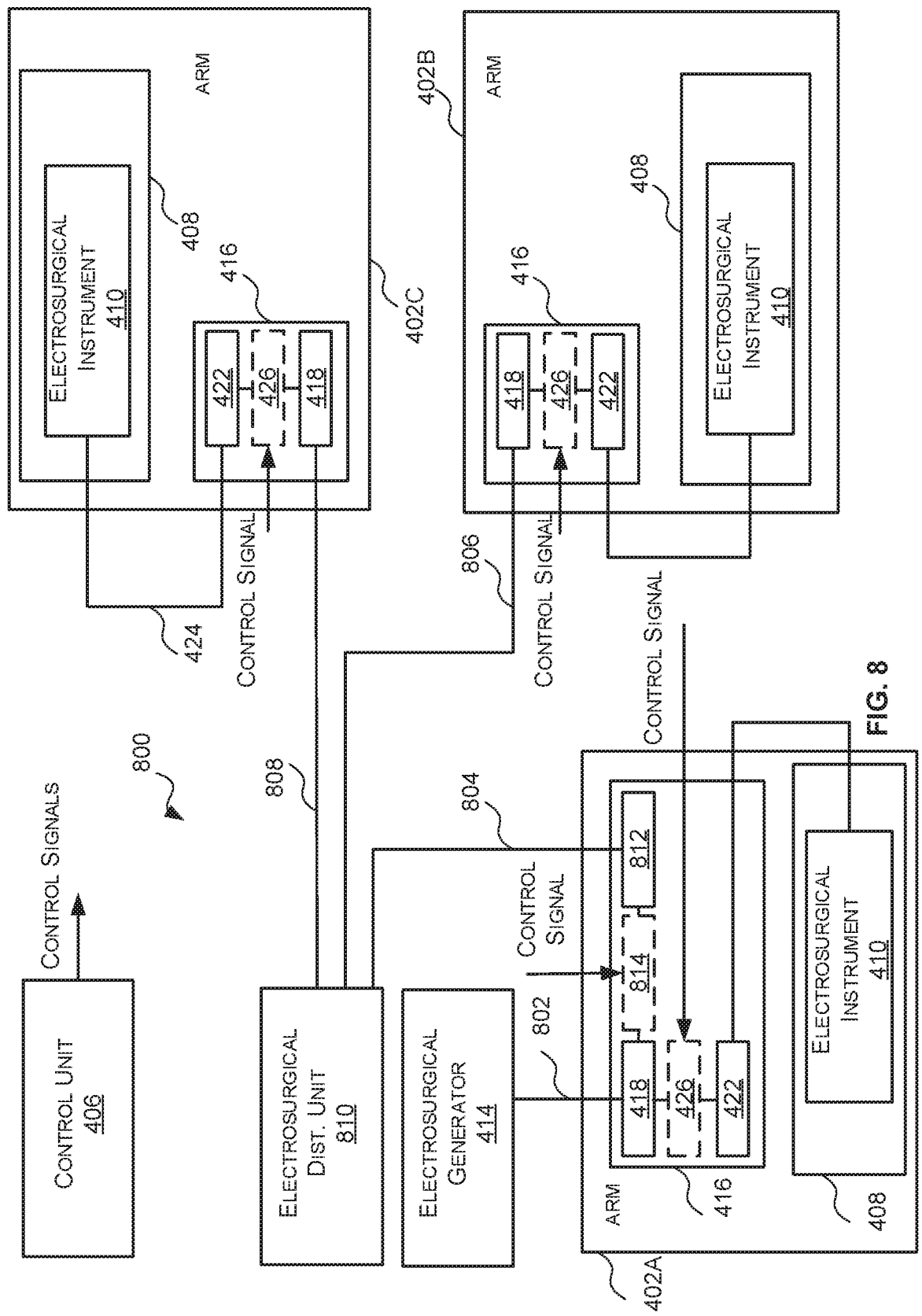
FIG. 8 is a schematic diagram of the electrosurgical system of FIG. 4 where the electrosurgical network has a third example star configuration.

Reference is now made to FIGS. 6 to 8 which illustrate example star configurations for the electrosurgical network 404.

FIG. 6 illustrates an electrosurgical system 600 wherein the electrosurgical network 404 has a first example star configuration. In this example, the electrosurgical network 404 comprises a plurality of links 602, 604 and 606 and each electrosurgical connection unit 416 is directly connected to the electrosurgical generator 414 via one of the links 602, 604, 606. Specifically, the electrosurgical connection unit 416 of the first robot arm 402A is connected to the electrosurgical generator 414 via the first link 602, the electrosurgical connection unit 416 of the second arm 402B is connected to the electrosurgical generator 414 via the second link 604, and the electrosurgical connection unit 416 of the third arm 402C is connected to the electrosurgical generator 414 via the third link 606.

In some cases, the electrosurgical generator 414 may not be able to control which links 602, 604, 606 receive a generated driving electrosurgical signal. As a result, any driving electrosurgical signal generated by the electrosurgical generator may be automatically transmitted over all links 602, 604, 606 connected to the electrosurgical generator 414. In other words all the links 602, 604, 606 are live or active. This means that in these cases all electrosurgical connection units 416 connected to the electrosurgical generator 414 receive any driving electrosurgical signal generated by the electrosurgical generator 414. Accordingly, to ensure that a driving electrosurgical signal generated by the electrosurgical generator 414 is only output from the output port(s) 422 attached to an electrosurgical instrument 410 which is to be controlled by the driving electrosurgical signal transmitted over the electrosurgical network 404 the electrosurgical connection units 416 comprise a switching unit 426 which controllably connects the input port 418 to the output port 422. The electrosurgical control unit 406 is then configured to transmit control signals to selected electrosurgical connection units 416 that cause the switching unit 426 of those electrosurgical connection units 416 to establish a connection between the corresponding input and output ports 418, 422.

In other cases, the electrosurgical generator 414 may be able to controllably transmit the generated electrosurgical signal over any selected combination of links 602, 604, 606 in response to a control signal (which may be generated by the control unit). For example, the electrosurgical generator 414 may be able to transmit a driving electrosurgical signal over only one of the links, over two of the links, or over all three of the links in response to a control signal. This allows the driving electrosurgical signal to only be provided to the electrosurgical connection units 416 which are connected to an electrosurgical instrument that is to be controlled by the driving electrosurgical signal. Accordingly, in these cases the electrosurgical control unit 406 may be configured to ensure that a driving electrosurgical signal generated by the electrosurgical generator 414 is only output from the output port(s) 422 attached to an electrosurgical instrument 410 which is to be controlled by the driving electrosurgical signal by transmitting a control signal to the electrosurgical generator 414 which causes the electrosurgical generator 414 to transmit a driving electrosurgical signal only over a selected set of links (which may be all, or only a portion of the links).

Where the electrosurgical generator 414 is capable of receiving a control signal and the electrosurgical connection units 416 comprise a switching unit 426 the electrosurgical control unit 406 may be configured to transmit control signals to the electrosurgical generator 414 and the electrosurgical connection units 416.

FIG. 7 illustrates an electrosurgical system 700 wherein the electrosurgical network 404 has a second example star configuration. In this example, the electrosurgical network 404 comprises a plurality of links 704, 706, 708 and the electrosurgical generator 414 is connected to an electrosurgical distribution unit 710 and each electrosurgical connection unit 416 is directly connected to the electrosurgical distribution unit 710 via one of the links 704, 706 or 708. Specifically, the electrosurgical connection unit 416 of the first arm 402A is connected to the electrosurgical distribution unit 710 via link 704, the electrosurgical connection unit 416 of the second arm 402B is connected to the electrosurgical distribution unit 710 via link 706, and the electrosurgical connection unit 416 of the third arm 402C is connected to the electrosurgical distribution unit 710 via link 708.

The electrosurgical distribution unit 710 is any device capable of receiving a driving electrosurgical signal from an electrosurgical output device and outputting the received driving electrosurgical signal to one or more electrosurgical input devices (devices capable of receiving a driving electrosurgical signal). The electrosurgical distribution unit 710 may comprise an input port for receiving an electrosurgical signal from an electrosurgical output device (in this example the input port is connected to an electrosurgical generator 414) and one or more output ports for outputting the received electrosurgical signal to an electrosurgical input device (in this example the output ports are connected to the input ports 418 of the electrosurgical connection units 416 via links 704, 706, 708), and the electrosurgical distribution unit 710 is configured to distribute the electrosurgical signal received on the input port to the output port(s). The input port may be permanently connected, or hardwired, to the output port(s) such that any driving electrosurgical signal received on the input port is automatically output on all output ports. Alternatively, the input port and the output port(s) may be controllably connected. For example, the electrosurgical distribution unit 710 may be able to controllably connect the input port to one or more output ports based on a control signal.

Similar to the example of FIG. 6, where the electrosurgical distribution unit 710 can controllably connect the input to one or more outputs the electrosurgical control unit 406 may be configured to transmit a control signal to the electrosurgical distribution unit so that the electrosurgical distribution unit 710 distributes a received driving electrosurgical signal to one or more selected links such that one or more of the links 704, 706, 708 are active and/or none, one or more than one of the links 704, 706, 708 are inactive. Where the electrosurgical connection units 416 comprise a switching unit 426 the electrosurgical control unit 406 may also, or alternatively, be configured to transmit a control signal to the electrosurgical connection units 416 to cause the connection between the input port 418 and output port 422 to be established for selected electrosurgical connection units 416.

The star configuration of FIG. 7 may provide advantages over the star configuration in FIG. 6 in cases where the electrosurgical generator 414 only comprises a single output port and/or the electrosurgical generator 414 is not capable of controlling which output ports receive a driving electrosurgical signal. In the latter case, the star configuration of FIG. 7 may allow certain links to be deactivated so that the electrosurgical connection units 416 that are not connected to an electrosurgical instrument to be controlled by the electrosurgical channel carried by the electrosurgical network 404 do not receive the driving electrosurgical signal for that electrosurgical channel.

FIG. 8 illustrates an electrosurgical system 800 wherein the electrosurgical network 404 has a third example star configuration. In this example, the electrosurgical network 404 comprises a plurality of links 802, 804, 806 and 808 and the electrosurgical generator 414 is connected to the electrosurgical connection unit 416 of one of the robot arms 402A, 402B and 402C (the first robot arm 402A in this example) via the first link 802, that electrosurgical connection unit 416 is also connected to an electrosurgical distribution unit 810 via the second link 804, and the remaining electrosurgical connection units 416 are directly connected to the electrosurgical distribution unit 810 via the remaining links 806, 808. Specifically, the electrosurgical connection unit 416 of the second arm 402B is directly connected to the electrosurgical distribution unit 810 via the third link 806, and the electrosurgical connection unit 416 of the third arm 402C is directly connected to the electrosurgical distribution unit 810 via the fourth link 808. Although FIG. 8 shows that the electrosurgical generator 414 is directly connected to the electrosurgical connection unit 416 of the first robot arm 402A, it will be evident to a person of skill in the art that this is an example only and that the electrosurgical generator 414 may be directly connected to the electrosurgical connection unit 416 of any of the robot arms 402A, 402B, 402C. The description of the electrosurgical distribution unit 710 above with respect to FIG. 7 equally applies to the electrosurgical distribution unit 810 of FIG. 8.

In this example, the electrosurgical connection unit 416 of the robot arm 402A that is directly connected to the electrosurgical generator 414 may comprise a second output port 812 which is connectable to the electrosurgical distribution unit 810. In some cases the second output port 812 may be configured to receive one or more cables that is/are connected to the electrosurgical distribution unit 810. The electrosurgical connection unit 416 is configured to output the driving electrosurgical signal received on the input port 418 (e.g. the electrosurgical signal received from the electrosurgical generator 414) on the second output port 812. In some cases, the input port 418 may be permanently connected, or hardwired, to the second output port 812 such that any driving electrosurgical signal received on the input port 418 is automatically output on the second output port 812. In other cases, however, the electrosurgical connection unit 416 may comprise a second switching unit 814 which is configured to controllably connect the input port 418 to the second output port 812 in response to a control signal. The electrosurgical network configuration shown in FIG. 8 may be advantageous where the electrosurgical generator 414 can be easily positioned near one of the robot arms 402A, 402B, 402C.

Similar to the example of FIG. 7, where the electrosurgical distribution unit 810 can controllably connect the input to one or more outputs the electrosurgical control unit 406 may be configured to transmit a control signal to the electrosurgical distribution unit 810 that causes the electrosurgical distribution unit 810 to connect the input to a selected set of outputs (which may be none, some or all of the outputs) such that none, one or both of links 806 and 808 are active. Where the electrosurgical connection units 416 comprise a switching unit 426 the electrosurgical control unit 406 may be configured to, in addition, or alternatively, transmit a control signal to the electrosurgical connection units 416 to cause the connection between the input port 418 and output port 422 to be established for selected electrosurgical connection units 416. Similarly, where an electrosurgical connection unit 416 comprises an additional switching unit 814 the electrosurgical control unit 406 may be configured to transmit a control signal to the electrosurgical connection unit 416 to cause the connection between the input port 418 and second output port 812 to be established or not.

Figure 9:
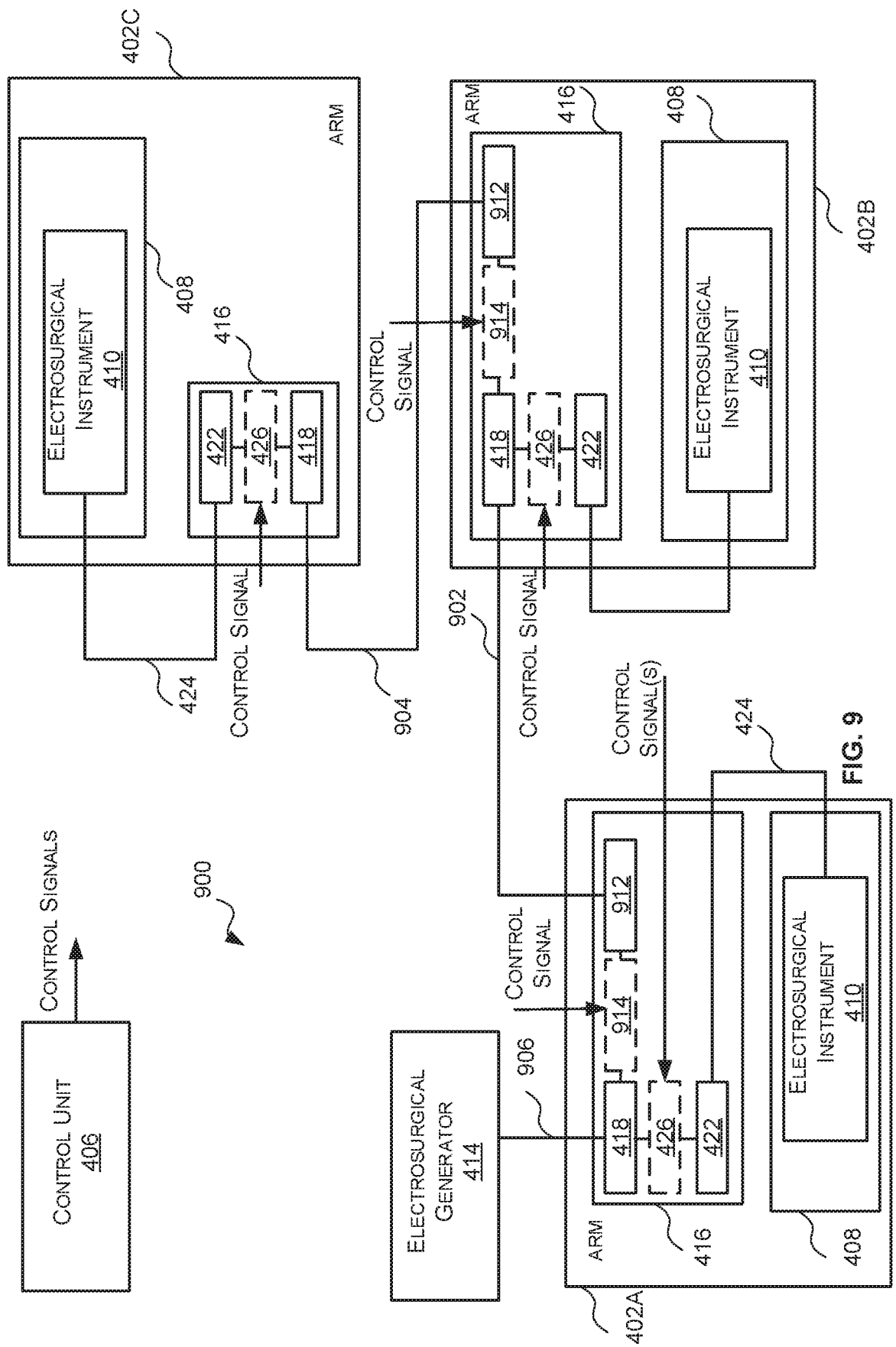
FIG. 9 is schematic diagram of the electrosurgical system of FIG. 4 where the electrosurgical network has a first example daisy-chain configuration.
Figure 10:
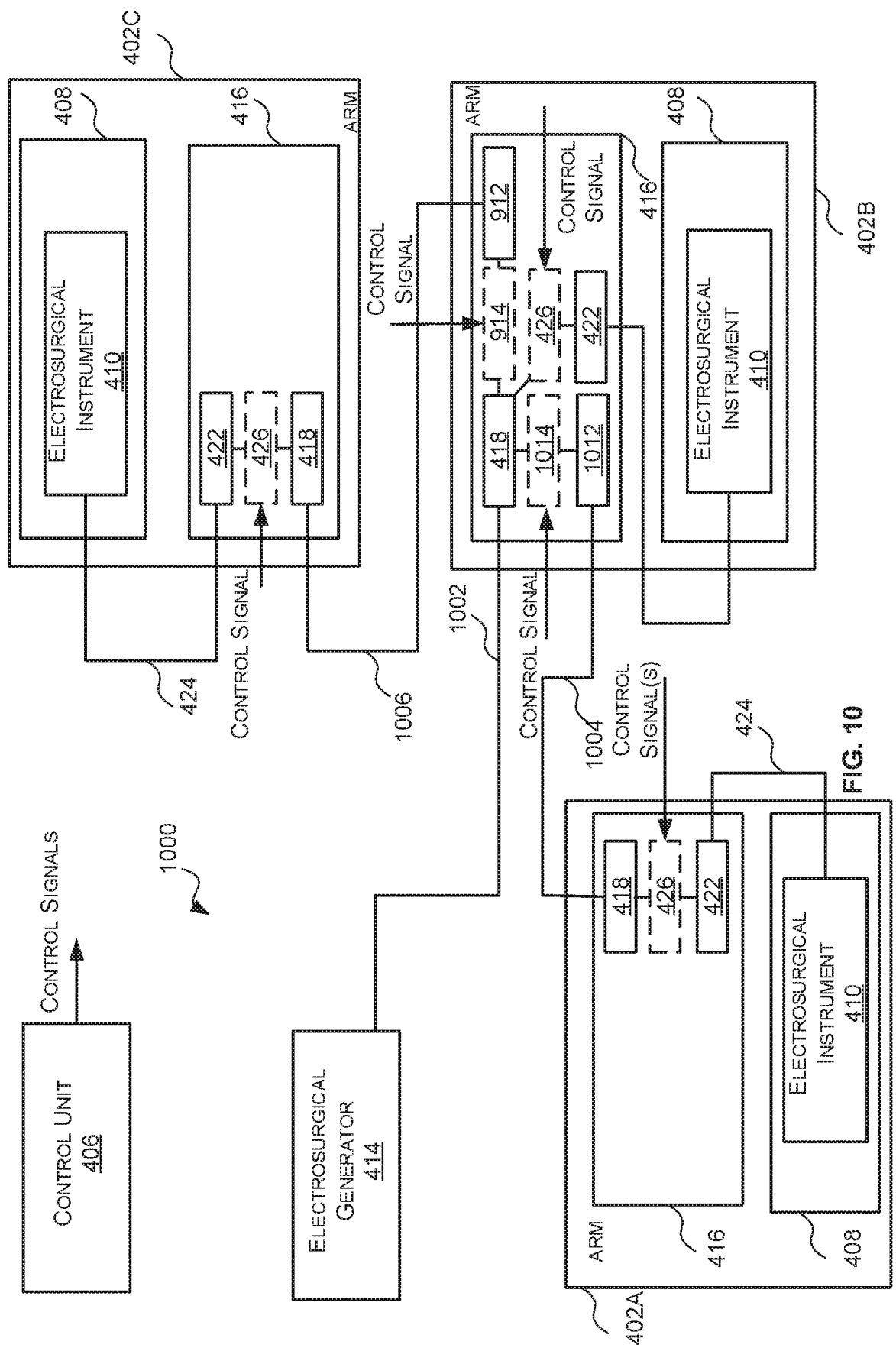
FIG. 10 is schematic diagram of the electrosurgical system of FIG. 4 where the electrosurgical network has a second example daisy-chain configuration.
Figure 11:
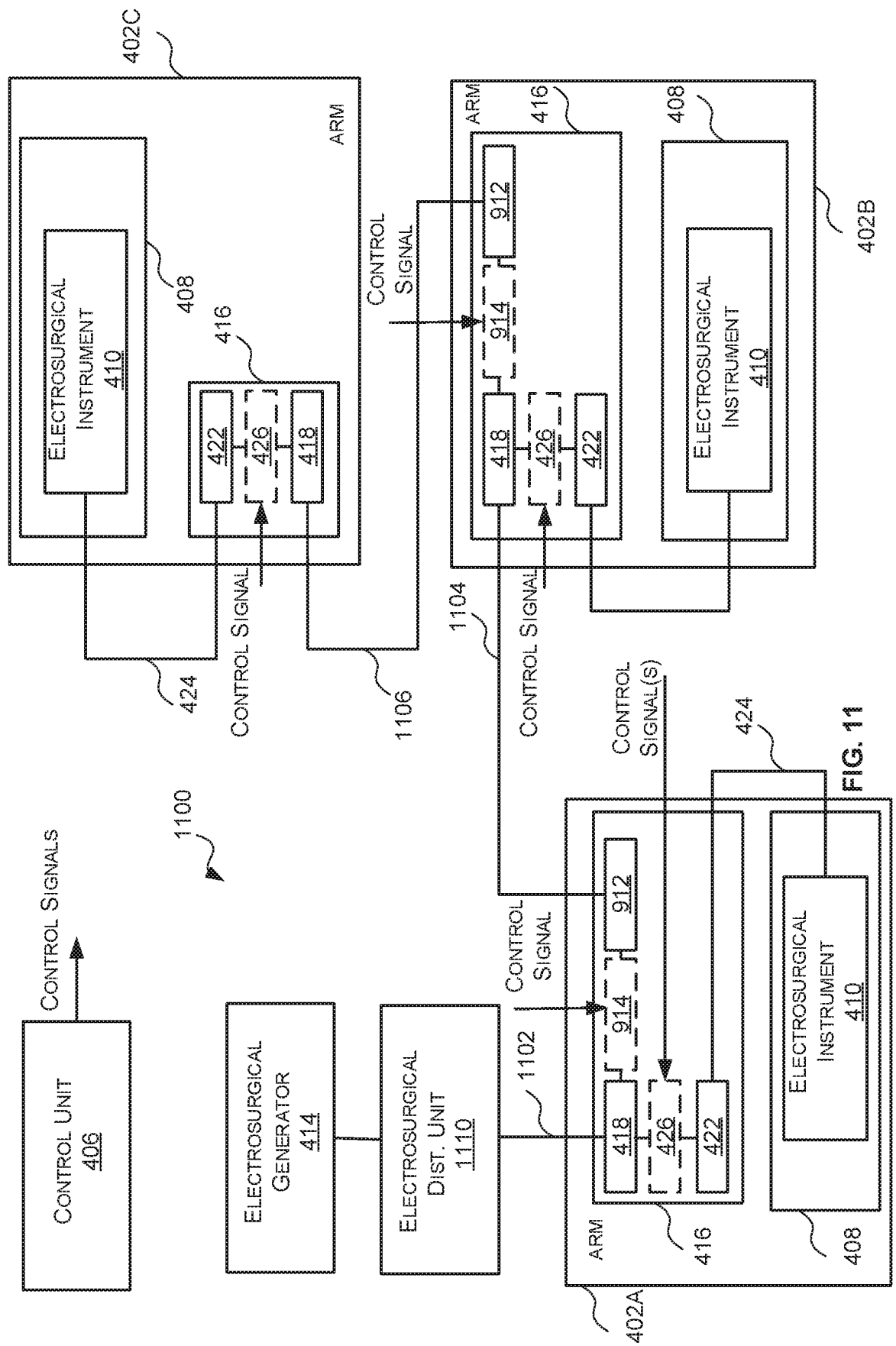
FIG. 11 is schematic diagram of the electrosurgical system of FIG. 4 where the electrosurgical network has a third example daisy-chain configuration.

Reference is now made to FIGS. 9 to 11 which illustrate electrosurgical systems 900, 1000, 1100 wherein the electrosurgical network 404 has exemplary daisy chain configurations. As briefly described above, in a daisy-chain configuration the electrosurgical connection units 416 are connected to each other in a serial sequence and one of the electrosurgical connection units 416 receives the driving electrosurgical signal for the electrosurgical channel (either from the electrosurgical generator 414 itself, or via an intermediate device, such as an electrosurgical distribution unit) and distributes the driving electrosurgical signal to the other electrosurgical connection units 416 via the chain. In these daisy-chain examples, one or more of the electrosurgical connection units 416 may comprise one or more additional output ports 912, 1012 to provide a received driving electrosurgical signal to another electrosurgical connection unit 416 in the chain. In such electrosurgical connection units 416 the input port 418 may be permanently connected, or hardwired, to the additional output ports 912, 1012 such that any driving electrosurgical signal received on the input port 418 is automatically sent out the additional output ports 912, 1012; or the electrosurgical connection units 416 may comprise one or more additional switching units 914, 1014 that are situated between the input port 418 and the additional output port(s) 912, 1012 that are configured to controllably connect the input port 418 to the additional output port(s) 912, 1012 in response to a control signal.

FIG. 9 illustrates an electrosurgical system 900 wherein the electrosurgical network 404 has a first example daisy-chain configuration. In this example, the electrosurgical network comprises a plurality of links 902, 904, 906 and the electrosurgical connection units 416 are daisy-chained via the links 902, 904 and the electrosurgical generator 414 is connected to the daisy-chain via link 906. Specifically, the electrosurgical connection unit 416 of the first arm 402A is connected to the electrosurgical connection unit 416 of the second arm 402B via link 902, and the electrosurgical connection unit 416 of the second arm 402B is connected to the electrosurgical connection unit 416 of the third arm 402C via link 904 to form a daisy chain of electrosurgical connection units 416. Once the electrosurgical connection units 416 have been daisy-chained, the driving electrosurgical signal can be provided to any of the electrosurgical connection units 416 in the chain and the driving electrosurgical signal can be distributed to the other electrosurgical connection units 416 via the chain.

In the example of FIG. 9 the electrosurgical generator 414 is directly connected to the electrosurgical connection unit 416 of the first arm 402A via link 906. Accordingly, in this example, the electrosurgical connection units 416 of the first and second arms 402A, 402B each comprise an additional output port 912 which is used to provide a driving electrosurgical signal received via the input port 418 to another electrosurgical connection unit 416 of the chain. Specifically, the electrosurgical connection unit 416 of the first arm 402A comprises an additional output port 912 which is connected to the input port 418 of the electrosurgical connection unit 416 of the second arm 402B so that the electrosurgical connection unit 416 of the first arm 402A can provide a driving electrosurgical signal received from the electrosurgical generator 414 via the input port 418 to the electrosurgical connection unit 416 of the second arm 402B; and the electrosurgical connection unit 416 of the second arm 402B comprises an additional output port 912 which is connected to the input port 418 of the electrosurgical connection unit 416 of the third arm 402C so that that the electrosurgical connection unit 416 of the second arm 402B can provide a driving electrosurgical signal received from the electrosurgical connection unit 416 of the first arm 402A via the input port 418 to the electrosurgical connection unit 416 of the third arm 402C.

Although FIG. 9 shows the electrosurgical generator 414 directly connected to the first arm 402A the electrosurgical generator 414 can be connected directly, or indirectly, to the electrosurgical connection unit 416 of any arm 402A, 402B or 402C. For example, FIG. 10 illustrates an electrosurgical system 1000 wherein the electrosurgical network 404 has a second example daisy-chain configuration. In this example, the electrosurgical network 404 comprises links 1002, 1004 and 1006. The daisy-chain configuration of FIG. 10 is the same as the daisy-chain configuration shown in FIG. 9 except that the electrosurgical generator 414 is directly connected to the electrosurgical connection unit 416 of the second arm 402B instead of being directly connected to the electrosurgical connection unit 416 of the first arm 402A. In this example, the electrosurgical connection unit 416 of the second arm 402B comprises two additional output ports 912, 1012 which are used to provide a received driving electrosurgical signal to the other electrosurgical connection units.

Specifically, the electrosurgical connection unit 416 of the second arm 402B comprises an additional output port 1012 which is connected to the input port 418 of the electrosurgical connection unit 416 of the first arm 402A so that that the electrosurgical connection unit 416 of the second arm 402B can provide the driving electrosurgical signal received from the electrosurgical generator 414, via its input port 418, to the electrosurgical connection unit 416 of the first arm 402A. The electrosurgical connection unit 416 of the second arm 402B also comprises a further additional output port 912 which is connected to the input port 418 of the electrosurgical connection unit 416 of the third arm 402C so that the electrosurgical connection unit 416 of the second arm 402B can provide a driving electrosurgical signal received from the electrosurgical generator 414 via its input port 418 to the electrosurgical connection unit 416 of the third arm 402C.

Furthermore, although FIGS. 9 and 10 show that the electrosurgical generator 414 is directedly connected to an electrosurgical connection unit 416 in the chain, in other examples the electrosurgical generator 414 may be indirectly connected to the chain. For example, FIG. 11 illustrates an electrosurgical system 1100 wherein the electrosurgical network 404 has a third example daisy-chain configuration. In this example, the electrosurgical network 404 comprises links 1102, 1104 and 1106. The daisy chain configuration shown in FIG. 11 is the same as the example daisy chain configuration shown in FIG. 9 except that the electrosurgical generator 414 is directly connected to an electrosurgical distribution unit 1110 and the electrosurgical distribution unit 1110 is connected to the input port 418 of the first arm 402A. Although FIG. 11 shows the electrosurgical distribution unit 1110 directly connected to the electrosurgical connection unit 416 of the first arm 402A it will be evident to a person of skill in the art that the electrosurgical distribution unit 1110 may be connected to any of the electrosurgical connection units 416. The configuration shown in FIG. 11 may provide advantages over the configurations shown in FIGS. 9-10 in cases where the electrosurgical generator 414 is not capable of controlling which output ports receive a driving electrosurgical signal.

In any of the daisy chain examples of FIGS. 9 to 11, to ensure that an electrosurgical signal output by the electrosurgical generator 414 is only output from the output port 422 of a desired set of arms 402A, 402B and/or 402C (which may include one, some or all the arms) the electrosurgical control unit 406 may be configured to transmit a control signal to one or more electrosurgical connection units 416 to cause the connection between the input port 418 and the output port 422 to only be established for selected electrosurgical connection units 416. For example, where only the first arm 402A is connected to an electrosurgical instrument 410 that is to be controlled by an electrosurgical channel carried by the electrosurgical network, the electrosurgical control unit 406 may generate one or more control signals which cause the switching unit 426 of the electrosurgical connection unit 416 of the first arm 402A to be enabled (i.e. such that a connection between the input port 418 and the output port 422 is established) and cause the switching unit 426 of the electrosurgical connection unit 416 of the other arms 402B and 402C to be disabled (i.e. such that a connection between the input port 418 and the output port 422 is not established).

Where one or more of the electrosurgical connection units 416 includes an additional switching unit 914, 1014 between the input port 418 and an additional output port 912, 1014 the electrosurgical control unit 406 may also be configured to transmit one or more control signals to the electrosurgical connection units 416 that cause only additional switching units 914, 1014 of selected arms 402A, 402B and/or 402C to be enabled so that an electrosurgical connection unit 416 doesn't receive a driving electrosurgical signal generated by the electrosurgical generator 414 unless that electrosurgical connection unit 416 needs to provide the driving electrosurgical signal to another electrosurgical connection unit 416 or needs to provide the driving electrosurgical signal to an electrosurgical instrument attached thereto. For example, in the configurations of FIGS. 9 and 10, if only the second arm 402B is attached to an electrosurgical instrument 410 that is to be controlled by the electrosurgical channel carried by the electrosurgical network 404 the electrosurgical control unit 406 may transmit one or more control signals to the electrosurgical connection units 416 that cause the additional switching unit 914 of the electrosurgical connection unit 416 of the first arm 402A to be active or enabled and cause the additional switching unit 914 of the second arm 402B to be disabled or inactive. This allows the driving electrosurgical signal generated by the electrosurgical generator 414 to be provided from the first arm 402A to the second arm 402B, but stops the driving electrosurgical signal from being transmitted from the second arm 402B to the third arm 402C.

Although the systems described above are described as connecting the electrosurgical connection units to a single electrosurgical channel, in other examples the electrosurgical connection units may be connected to multiple electrosurgical channels. Each channel may carry a different driving electrosurgical signal. This may allow different driving electrosurgical signals to be easily provided to an electrosurgical instrument attached to the arm without reconfiguring the electrosurgical generator. This may alternatively, or in addition, allow different driving electrosurgical signals to be provided to different electrosurgical instruments simultaneously. For example, this may allow an electrosurgical instrument attached to a first arm (e.g. arm 402A) to be driven by a first driving electrosurgical signal and an electrosurgical instrument attached to a second arm (e.g. arm 402B) to be simultaneously driven by a second driving electrosurgical signal. All the channels may be controlled by the same electrosurgical generator or two or more channels may be controlled by different electrosurgical generators. Example electrosurgical systems in which the electrosurgical connection units 416 are connected to multiple electrosurgical channels are described with reference to FIGS. 12-14.

Figure 12:
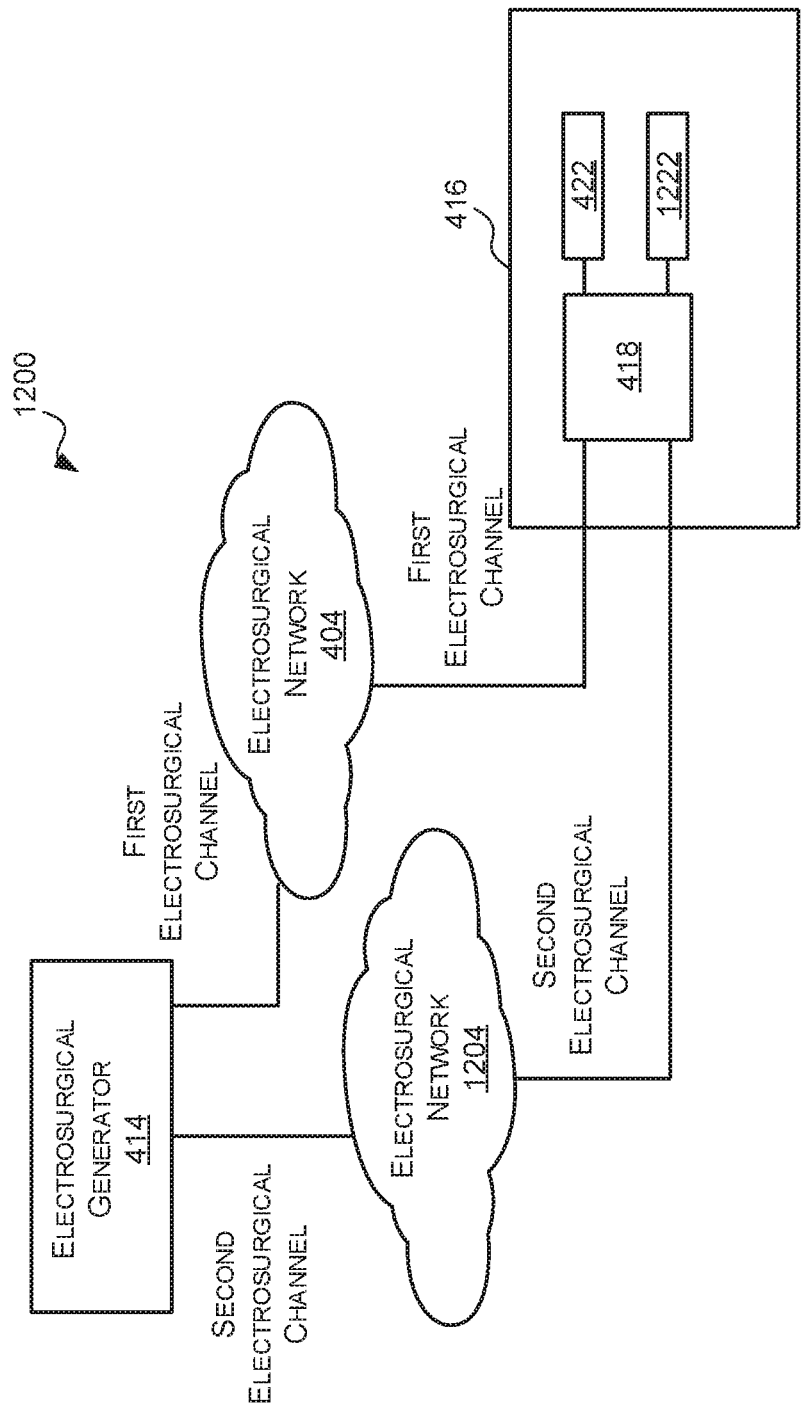
FIG. 12 is a schematic diagram of a first example electrosurgical system in which the electrosurgical connection units are connected to multiple electrosurgical channels.

Reference is now made to FIG. 12 which shows a first example electrosurgical system 1200 in which the electrosurgical connection units 416 are connected to multiple electrosurgical channels. In this example, a single electrosurgical connection unit 416 is illustrated for ease of explanation, but it will be evident to a person of skill in the art that multiple electrosurgical connection units 416 may be connected to the electrosurgical networks 404, 1204 in accordance with any of the configurations described above. In this example, there are two electrosurgical networks 404, 1204 which statically connect the electrosurgical connection units 416 to two electrosurgical channels. Specifically, the first electrosurgical network 404 connects the electrosurgical connection units 416 to a first electrosurgical channel and the second electrosurgical network 1204 connects the electrosurgical connection units 416 to a second electrosurgical channel. The electrosurgical channels may be the same type or may be different types. For example, there maybe two monopolar channels, two bipolar channels, or a monopolar channel and a bipolar channel. The electrosurgical networks 404, 1204 may have any of the configurations (e.g. star, daisy-chained) described above.

The electrosurgical connection units 416 comprise an input port 418 which is connected to both electrosurgical networks 404, 1204, and one output port 422 and 1222 per electrosurgical channel. The first electrosurgical channel received via the input port 418 is connected to the first output port 422 such that a driving electrosurgical signal received on the first channel is output on the first output port 422, and the second electrosurgical channel received via the input port 418 is connected to the second output port 1222 such that a driving electrosurgical signal received via the second electrosurgical channel is output on the second output port 1222. In this example an electrosurgical instrument attached to the arm can be manually connected to one of the output ports 422 or 1222. Although not shown in FIG. 12 the electrosurgical connection units 416 may comprise one or more switching units between the input port 418 and output ports 422, 1222 which controllably connect the first and second channels received via the input port 418 to the output ports 422, 1222 in response to a control signal (which may be generated by the control unit).

Figure 13:
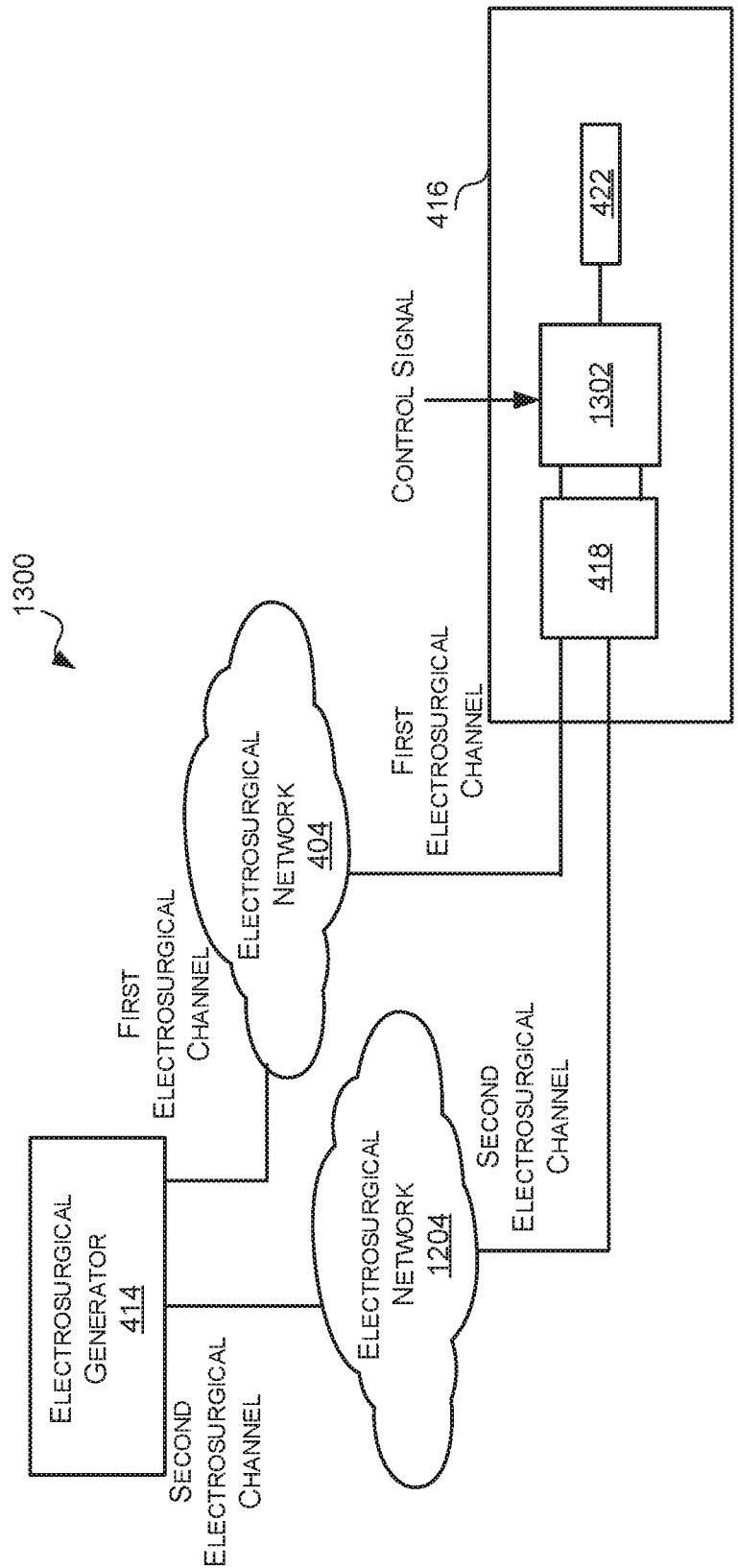
FIG. 13 a schematic diagram of a second example electrosurgical system in which the electrosurgical connection units are connected to multiple electrosurgical channels.

Reference is now made to FIG. 13 which shows a second example electrosurgical system 1300 in which the electrosurgical connection units 416 are connected to multiple electrosurgical channels. This example is the same as the example shown in FIG. 12 except that instead of the electrosurgical connection units 416 comprising an output port per electrosurgical channel there is a single output port 422 and the electrosurgical connection units 416 comprise a switching unit 1302 which controllably connects one (or none) of the first and second channels to the output port 422 in response to a control signal (which may be generated by the electrosurgical control unit 406). This allows an electrosurgical instrument attached to an arm to be dynamically connected to the first electrosurgical channel or the second electrosurgical channel without having to disconnect and reconnect the electrosurgical instrument to the electrosurgical connection unit 416. In this example the first and second electrosurgical channels are typically of the same type (e.g. the first and second electrosurgical channels are bipolar channels or the first and second channels are monopolar channels).

In other examples, the electrosurgical connection units may support a combination of the configurations shown in FIGS. 12 and 13. For example, the electrosurgical connection units 416 may receive three different channels via one or more electrosurgical networks and two of the electrosurgical channels may be of the same type which are controllably connected to a first output port, and the third electrosurgical channel may be of a different type which is directly or controllably connected to a second output port.

In some cases, instead of the wires of the electrosurgical links being dedicated to a particular channel as in FIGS. 12 and 13, the wires of the electrosurgical links of the electrosurgical network may be dynamically allocated to one of a plurality of channels. For example, reference is now made to FIG. 14 which illustrates a third example electrosurgical system 1400 in which the electrosurgical connection units 416 are connected to multiple electrosurgical channels. In this example, there is a single electrosurgical network 404 and each electrosurgical link 1402, 1404 of the electrosurgical network 404 comprises a plurality of electrosurgical wires or conductors 1406, 1408, 1410, 1412, 1414, 1416, 1418, 1420 which are dynamically allocated to one of a plurality of channels 1422, 1424, 1426, 1428, 1430, 1432. Specifically, the electrosurgical system 1400 of FIG. 14 comprises an electrosurgical multiplexer (MUX) 1434 which receives a plurality of electrosurgical channels 1422, 1424, 1426, 1428, 1430, 1432 and controllably connects one or more of the electrosurgical channels 1422, 1424, 1426, 1428, 1430, 1432 to one or more of the wires of the electrosurgical links in response to a control signal (which may be generated and transmitted by the control unit). Such a system allows a plurality of electrosurgical channels to be dynamically allocated to different electrosurgical instruments.

Figure 14:
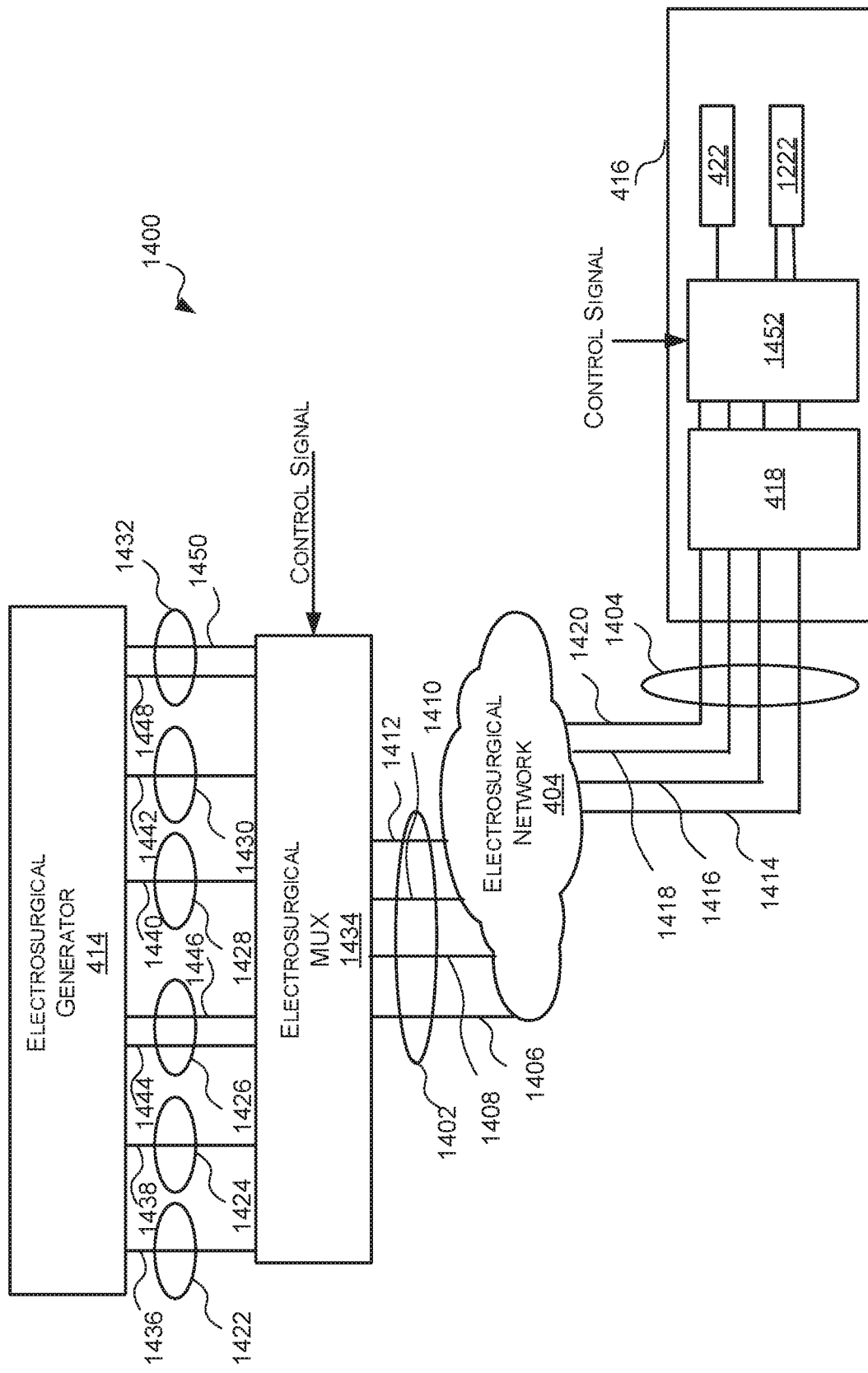
FIG. 14 a schematic diagram of a third example electrosurgical system in which the electrosurgical connection units are connected to multiple electrosurgical channels.

In the example of FIG. 14 the electrosurgical MUX 1434 is configured to receive six electrosurgical channels 1422, 1424, 1426, 1428, 1430, 1432 and each link 1402 comprises four wires 1406, 1408, 1410, 1412, 1414, 1416, 1418, 1420, however, it will be evident to a person of skill in the art that the techniques and principles described herein may be used where there are more than six electrosurgical channels or less than six electrosurgical channels, and/or the links have more than four wires or less than four wires.

The number of wires associated with each electrosurgical channel may be based on the type of electrosurgical channel. For example, monopolar electrosurgical channels may be associated with a single wire to transmit the driving electrosurgical signal to the electrosurgical switching units (and thus to the electrosurgical instrument attached thereto) and bipolar electrosurgical channels may be associated with two wires—a first wire to transmit the driving electrosurgical signal to the electrosurgical connection units (and thus to the electrosurgical instrument attached thereto) and a second wire to transmit the return electrosurgical signal from the electrosurgical connection unit to the electrosurgical generator. All of the electrosurgical channels may be of the same type or they may be a combination of different types. In the example of FIG. 14 there are four monopolar electrosurgical channels 1422, 1424, 1428 and 1430 each associated with a single wire 1436, 1438, 1440, 1442 and two bipolar electrosurgical channels 1426, 1432 each associated with two wires 1444, 1446, 1448, 1450, however, it will be evident to a person of skill in the art that this is an example only and that other systems may comprise another number of electrosurgical channels and the channels may be associated with a different number of wires.

In the example of FIG. 14 the electrosurgical channels 1422, 1424, 1426, 1428, 1430, 1432 are controlled by a single electrosurgical generator 414 (i.e. a single electrosurgical generator 414 generates the driving electrosurgical signal and, optionally receives the return electrosurgical signal, for the channel), however, in other examples one or more of the electrosurgical channels may be controlled by different electrosurgical generators. For example, the first three electrosurgical channels 1422, 1424, 1426 may be controlled by a first electrosurgical generator and the last three electrosurgical channels 1428, 1430, 1432 may be controlled by a second, different, electrosurgical generator.

As described above, the electrosurgical MUX 1434 is configured to dynamically map one or more of the electrosurgical channels 1422, 1424, 1426, 1428, 1430, 1432 to one or more of wires of the electrosurgical links of the electrosurgical network. The phrase "mapping an electrosurgical channel to one or more wires of the electrosurgical links" is used herein to mean that the one or more wires of the channel are electrically connected to one or more wires of the electrosurgical links of the electrosurgical network so as to connect the channel to the electrosurgical connection units 416. For example, in response to a control signal the electrosurgical MUX 1434 may electrically connect the wire 1436 of the first channel 1422 to the first wire 1406 of the electrosurgical links 1402, and electrically connected the wires 1444 and 1446 of the third channel 1426 to the third and fourth wires 1410 and 1412 of the electrosurgical links 1402 so that the electrosurgical connection units 416 are connected to the first and third channels 1422 and 1426.

The number of channels that can be mapped to the wires 1406, 1408, 1410, 1412, 1414, 1416, 1418, 1420 of the electrosurgical links at any one time depends on the number of wires per link and the number of wires per channel. For example, in cases where each link comprises four wires, monopolar channels are associated with only one wire and bipolar channels are associated with two wires then the electrosurgical MUX 1435 may be able to map up to four monopolar channels; up to two bipolar channels; or a bipolar channel and up to two monopolar channels to the four wires of the electrosurgical links. In many cases only two instruments can be controlled by the same command interface at the same time. However, in some cases there may a second command interface that can be used to control an additional two instruments. The system 1400 shown in FIG. 14 could be used in a single command interface case or a dual command interface case as it would allow up to four monopolar instruments to be controlled or driven by different electrosurgical channels.

As described above, the electrosurgical connection units 416 comprise an input port 418 which is connected to an electrosurgical link 1404 of the electrosurgical network. The input ports 418 are coupled to wires or conductors which correspond to the wires or conductors of a link of the electrosurgical network such that when the input port 418 is connected to the link the wires of the electrosurgical connection unit are connected to the corresponding wires of the electrosurgical link. To be able to adjust to the dynamic mapping of electrosurgical channels to wires of the electrosurgical links of the electrosurgical network each electrosurgical connection unit 416 comprises an electrosurgical switching unit 1452 that is configured to controllably connect one or more wires of the input port 418 to one or more wires of the output ports 422, 1222 in response to a control signal (which may be generated by the control unit).

For example, when an electrosurgical connection unit 416 is connected to an electrosurgical instrument that is to be controlled by the first electrosurgical channel 1422 and the first electrosurgical channel 1422 has been mapped to the first wire 1406, 1414 of the electrosurgical links the electrosurgical switching unit 1452 may receive a control signal which causes the electrosurgical switching unit 1452 to electrically connect the first wire 1414 of the input port 418 to a first wire of the first output port 422. Where either a monopolar electrosurgical instrument or a bipolar electrosurgical instrument may be connected to the arm the electrosurgical connection units 416 may comprise two output ports 422 and 1222, one output port 422 for monopolar electrosurgical instruments and the other output port 1222 for bipolar electrosurgical instruments. In these cases, the electrosurgical switching unit 1452 may be able to electrically connect wires of the input port 418 associated with a monopolar channel to the first output port 422 and may be able to electrically connected wires of the input port 418 associated with a bipolar channel to the second output port 1222.

The control signals that are transmitted to the electrosurgical MUX and the electrosurgical switching unit 1452 may be generated by the electrosurgical control unit 406. In some cases, the electrosurgical control unit 406 may be configured to generate the control signal(s) that cause the electrosurgical MUX 1434 to map a particular channel to one or more wires of the electrosurgical link to which it is connected in response to receiving information that an electrosurgical instrument has been selected for use on a particular arm 402A, 402B or 402C. In other cases, the electrosurgical control unit 406 may be configured to generate the control signal(s) that cause the electrosurgical MUX to map a particular channel to one or more wires of the electrosurgical link in response to receiving information that indicates that activation of a particular electrosurgical instrument is requested.

The system of FIG. 14 not only allows different electrosurgical channels to be dynamically allocated to electrosurgical instruments but also provides the possibility of an alternative path through the electrosurgical network for an electrosurgical channel should there be an issue with the current path through the electrosurgical network. For example, if one of the electrosurgical wires or conductors currently allocated to a particular electrosurgical channel fails (e.g. the wire or conductor stops conducting) it would be possible to re-route the electrosurgical signal through a different set of electrosurgical wires or conductors through the network. In some cases, it may be possible to test each wire in a link after use to identify broken wires or conductors. The electrosurgical control unit 406 could then mark any broken wires or conductors as faulty and assign electrosurgical signals around it. The electrosurgical control unit 406 may be configured to refuse a request if a predetermined number of wires or conductors are broken.

In any of the systems (e.g. 1200, 1300, 1400) where the electrosurgical connection units 416 are connected to multiple electrosurgical channels it is possible to have multiple electrosurgical instruments in use at any one time, each controlled by a different electrosurgical channel. To ensure that multiple electrosurgical instruments do not interfere with each other the electrosurgical control unit 406 may be configured to ensure that they are activated in a suitable sequence. For example, using multiple electrosurgical instruments too close together may cause interference and damage. Having multiple electrosurgical instruments being triggered simultaneously may also cause damage. Accordingly, the electrosurgical control unit 406 may be configured to limit how the instruments may be used together. For example, the electrosurgical control unit 406 may prevent multiple electrosurgical instruments from being triggered simultaneously or prevent them from being triggered if their end effectors are too close together.

In any of the systems described above (e.g. 400, 600, 700, 800, 900, 1000, 1100, 1200, 1300, 1400), or in any combination thereof, the electrosurgical control unit 406 may be able to dynamically detect the location of the electrosurgical generator 414 in the electrosurgical network 404 and/or the configuration of the electrosurgical network 404 based on, for example, information received from the electrosurgical connection units 416, an electrosurgical distribution unit 710, 810, 1110, an electrosurgical MUX 1434 or the electrosurgical generator 414 itself and may dynamically enable/disable certain links and/or input-output port connections based on the detected location of the electrosurgical generator and/or the configuration of the electrosurgical network 404.

For example, in some cases the electrosurgical connection units 416 may be able to mechanically, electrically, optically or magnetically sense when an electrosurgical cable has been inserted into a port thereof and may transmit this information to the electrosurgical control unit 406. Specifically, one or more ports of the electrosurgical connection units may comprise: a mechanical sensor (such as, but not limited to, a microswitch) that is able detect when an electrosurgical cable has been plugged therein; an electrical sensor (such as, but not limited to, electrical circuitry connected to one or more pins thereof) that can detect a change in impedance or a change in voltage indicating a cable is connected thereto; an optical sensor (such as, but not limited to, an optical sensor that comprises a light transmitter and light receiver) that is able to detect when an electrosurgical cable is plugged therein by the light receiver detecting light from the light transmitter or detecting the absence of light from the light transmitter; or a magnetic sensor (such as, but limited to, a hall effect sensor) that is able to detect when an electrosurgical cable is plugged therein by detecting the presence of a magnetic field.

In some cases, one or more of the electrosurgical connection units 416 may comprise a plurality of ports over which a driving electrosurgical signal may be received and depending on the configuration of the electrosurgical network any of those ports may be considered the input port 418. For example, as described in more detail below, one or more of the electrosurgical connection units 416 may comprises an electrosurgical generator port that is configured to receive an electrosurgical generator cable, which is configured to directly connect the electrosurgical connection unit to an electrosurgical generator 414; and one or more other ports which are configured to receive an electrosurgical connector cable, which is used to connect the electrosurgical connection unit to any other device in the electrosurgical network, such as another electrosurgical connection unit 416 or an electrosurgical distribution unit 710, 810, 1110. As will be described in more detail below, in some examples the first cable may only be capable of transmitting electrosurgical signals (e.g. a driving electrosurgical signal) and the second cable may be capable of concurrently transmitting electrosurgical signals and data signals (e.g. control signals). A cable capable of concurrently transmitting electrosurgical signals and data signals is referred to herein as an electrosurgical/data cable.

In the cases where an electrosurgical connection unit 416 has an electrosurgical generator port, the electrosurgical connection unit 416 may comprise an electrosurgical generator cable detection unit (not shown) that is configured to detect when an electrosurgical generator cable has been inserted into, or plugged into, the electrosurgical generator port. The electrosurgical generator cable detection unit may comprise any of the sensors described above (e.g. electrical, mechanical, optical or magnetic etc.) to detect when a cable has been inserted into the electrosurgical generator port. In some cases, the electrosurgical generator cable detection unit may be configured to detect when specifically an electrosurgical generator cable has been inserted into or plugged into the electrosurgical generator port. For example, an electrosurgical generator cable may have a component that interacts with, or is detectable by, a corresponding component of the electrosurgical generator cable detection unit. For example, the electrosurgical generator cable detection unit may comprise an optical receiver and an optical transmitter that are configured such that the optical receiver is only able to receive light from the optical transmitter when an electrosurgical generator cable that comprises a light pipe or channel is plugged into the electrosurgical generator port. Alternatively, the electrosurgical generator cable detection unit may comprise a magnetic sensor (e.g. hall effect sensor) that is configured to sense a magnetic field generated by a magnetic in an electrosurgical generator cable, or the electrosurgical generator may comprise an electric sensor that is configured to sense a change in impedance when an electrical conductor of an electrosurgical generator cable is inserted into the electrosurgical generator port.

In other cases, the electrosurgical generator cable detection unit may be configured to simply detect when any cable has been inserted into or plugged into electrosurgical generator port based on the assumption that only an electrosurgical generator cable can be, or would be, plugged into the electrosurgical generator port. For example, the electrosurgical generator cable detection unit may comprise an optical sensor comprising an optical transmitter and optical receiver configured such that the optical receiver will receive light from the optical transmitted unless a cable is plugged into the input port and blocks the transmitter light from reaching the receiver. In some cases, this may allow the electrosurgical generator cable detection unit to be simpler than in the case where the electrosurgical generator cable is configured to detect an electrosurgical generator cable specifically. In some cases, to ensure that only an electrosurgical generator cable can be plugged into the electrosurgical generator port, the electrosurgical generator port may be keyed with a mechanical component (e.g. keyway) which prevents mating except with a cable which has a correctly oriented matching connector.

If an electrosurgical connection unit 416 detects that an electrosurgical generator cable has been inserted into the electrosurgical generator port thereof the electrosurgical connection unit 416 may notify the electrosurgical control unit 406. Example mechanisms by which the electrosurgical connection unit 416 may notify the electrosurgical control unit 406 are provided below. In response to receiving such a notification the electrosurgical control unit 406 may be able to detect the location of the electrosurgical generator in the electrosurgical network 404 and generate and transmit control signals to the devices in the electrosurgical network 404 to connect a selected set of one or more output ports 422 to the electrosurgical channel based on the detected location.

In other examples, the input ports 418 may comprise a driving electrosurgical signal detection unit. In these cases, when the system is operating in a test mode, the electrosurgical control unit 406 may send a request to every electrosurgical connection unit to request an input from the electrosurgical generator while at the same time ensuring no output ports 422 are connected to the corresponding input port 418. Each driving electrosurgical signal detection unit would then 'listen' for a driving electrosurgical signal. If a driving electrosurgical signal detection unit of an electrosurgical connection unit 416 detects a driving electrosurgical signal the electrosurgical connection unit 416 may notify the electrosurgical control unit 406. Example mechanisms by which an electrosurgical connection unit 416 may notify the electrosurgical control unit 406 are provided below. In response to receiving such a notification the electrosurgical control unit 406 may be able to detect the location of the electrosurgical generator 414 in the electrosurgical network 404 and generate and transmit control signals to the devices in the electrosurgical network 404 to connect a selected set of one or more output ports 422 to the electrosurgical channel based on the detected location.

In some cases, an electrosurgical connection unit 416 may be configured to notify the electrosurgical control unit 406 that it has detected an electrosurgical generator connected to the electrosurgical channel (e.g. an electrosurgical connection unit 416 has detected an electrosurgical generator cable has been plugged into the electrosurgical generator port thereof; or the electrosurgical connection unit 416 has detected a driving electrosurgical signal on the input port 418 during a test mode or phase) by transmitting a message or control signal to the electrosurgical control unit 406. In some cases, the electrosurgical connection unit 416 may transmit the message or control signal via the same data communication network or channel by which the control unit transmits control signals to the electrosurgical connection unit 416 to control the connection of the output port 422 to the electrosurgical channel. In some cases, the electrosurgical connection unit 416 may be configured to periodically receive messages or data packets from the electrosurgical control unit 406 and may notify the electrosurgical control unit 406 of such a detection by: modifying one of the received messages or data packets to indicate that the electrosurgical connection unit 416, and transmitting the modified message or data packet to the electrosurgical control unit 406. In some cases, modifying a received message or data packet may comprise setting a particular flag in the received message or data packet. In other cases, the electrosurgical connection unit 416 may be configured to notify the electrosurgical control unit that it has detected an electrosurgical generator connected to the electrosurgical channel by sending a special control signal or message to the electrosurgical control unit 406 that indicates that the detection has been made and the specific electrosurgical connection unit 416 that made the detection.

In some cases, any of the electrosurgical distribution units and/or electrosurgical multiplexors in the system may be configured in a similar manner as the electrosurgical connection units with an electrosurgical generator cable detection unit and/or an electrosurgical signal detection unit to detect when an electrosurgical generator is connected to the electrosurgical channel. In a similar manner as the electrosurgical connection units, when an electrosurgical generator cable detection unit or an electrosurgical signal detection unit of an electrosurgical distribution unit or electrosurgical multiplexor detects that an electrosurgical generator is connected to the electrosurgical channel the electrosurgical distribution unit or the electrosurgical multiplexor may notify the electrosurgical control unit 406.

In some cases, in addition to, or alternatively to, the electrosurgical connection units 416. the electrosurgical distribution units 710, 810, 1110 and/or the electrosurgical multiplexors 1434 in the electrosurgical network 414 being able to detect that an electrosurgical generator is connected to the electrosurgical channel and notify the control unit thereof, the electrosurgical generator may itself may able to detect that it is connected to the electrosurgical channel. For example, as described above, in some cases the electrosurgical generator may be able to communicate with the control unit. For example, the electrosurgical generator may be connected to the robot control system used to control the robot arm. As described above, this may allow the surgeon, or other user, to select waveform(s) to be produced by the electrosurgical generator and the configuration of the selected waveform(s) may then be transmitted to the electrosurgical generator via the robot control system which cause the electrosurgical generator to configure itself to generate a current with the configured waveform(s). In these cases, the electrosurgical generator may itself be configured to notify the electrosurgical control unit 406 that it is connected to the electrosurgical channel. For example, as described in more detail below, in some cases the same cables may be used to carry electrosurgical signals between the devices of the electrosurgical network and data/control signals between the device of the electrosurgical network. In these cases, when a device (e.g. electrosurgical connection unit) is connected to the electrosurgical network that device may be allocated a unique identifier (e.g. address) on the network that indicates the location of the device in the network. Once an electrosurgical generator is connected to the network and has been allocated a unique address it may send a message/data packet/control signal to the electrosurgical control unit 406 indicating its unique address and some other information uniquely identifying the electrosurgical generator. Upon receipt of such a message/data packet/control signal the electrosurgical control unit 406 may be configured to identify the location of the electrosurgical generator. The electrosurgical control unit 406 may then generate control signals based on the detected location of the electrosurgical generator so that a selected set of one or more output ports 422 are connected to the electrosurgical channel.

In some cases, the electrosurgical control unit 406 may be configured to only allow one electrosurgical generator to be connected to the same electrosurgical channel at the same time. For example, the electrosurgical control unit 406 may be configured to give precedence to the first electrosurgical generator that is connected to an electrosurgical channel. Specifically, the electrosurgical control unit 406 may be configured such that, once it has been notified by a device on the electrosurgical network 404 (e.g. an electrosurgical connection unit, electrosurgical distribution unit, or an electrosurgical generator) that the device has detected an electrosurgical generator connected to the electrosurgical channel, if the electrosurgical control unit 406 subsequently receives a notification from another device on the electrosurgical network 404 (e.g. an electrosurgical connection unit, electrosurgical distribution unit, or an electrosurgical generator) that it has also detected an electrosurgical generator connected to the electrosurgical channel, the electrosurgical control unit 406 will not electrically connect that electrosurgical generator to any of the output ports 422. In other examples, the electrosurgical control unit 406 may be configured to give precedence to an electrosurgical generator connected to a central electrosurgical distribution unit over an electrosurgical generator connected to an electrosurgical connection unit 416. In other cases, the electrosurgical control unit 406 may be configured to allow multiple electrosurgical generators to be connected to the same electrosurgical channel at the same time, but the electrosurgical control unit 406 may be configured to restrict use of each of the electrosurgical generators to a subset of the output ports 422 (i.e. the electrosurgical generator may only be electrically connectable to a subset of the output ports 422). For example, if there are multiple electrosurgical generators connected to the same electrosurgical channel via different electrosurgical connection units then the control unit may restrict the use of each electrosurgical generator to the output port 422 of the electrosurgical connection unit to which it is connected.

Figure 15:
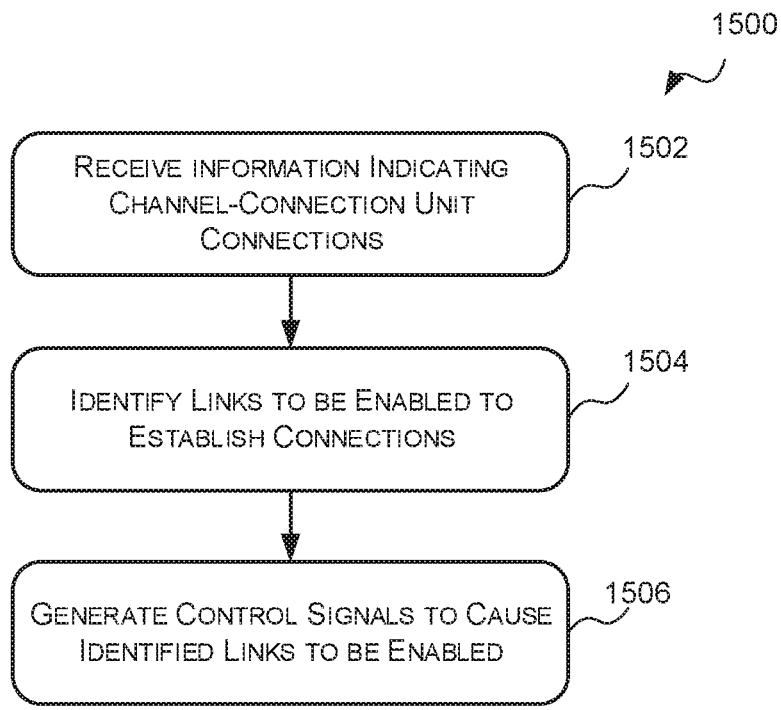
FIG. 15 is a flow diagram of a first example method to control which output ports of the electrosurgical connection units are connected to which electrosurgical channels.
Figure 16:
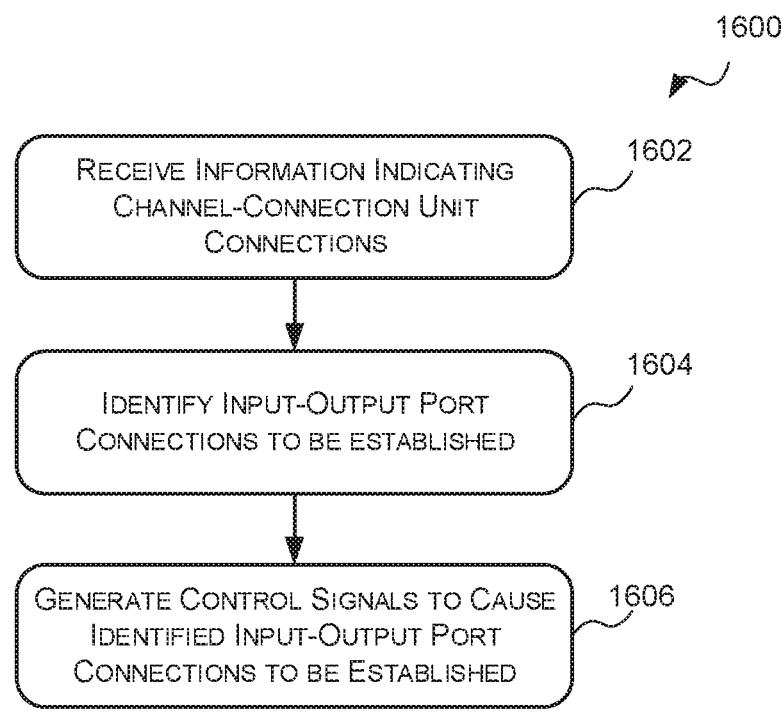
FIG. 16 is a flow diagram of a second example method to control which output ports of the electrosurgical connection units are connected to which electrosurgical channels.

Reference is now made to FIGS. 15 and 16 which illustrate example methods which may be implemented by the electrosurgical control unit 406 to control the operation of the electrosurgical output device (e.g. electrosurgical generator 414, electrosurgical distribution unit 710, electrosurgical distribution unit 810) and/or the electrosurgical connection units 416 to cause an electrosurgical connection to be established between the electrosurgical output device and the output port of a selected combination of electrosurgical connection units 416.

FIG. 15 illustrates a first example method 1500 which may be implemented by the electrosurgical control unit 406 to control which output ports 422 are connected to which electrosurgical channels. In this first example method 1500 the control unit is configured to cause an electrosurgical connection to be established between the electrosurgical output device and the output port of a selected combination of electrosurgical connection units by selectively enabling and disabling all or portion of links of the electrosurgical network 404. The method 1500 begins at block 1502 where the electrosurgical control unit 406 receives information indicating which electrosurgical connection units are to be connected to which electrosurgical channels. Where there is only one electrosurgical channel that is transported via the electrosurgical network, the information indicating which electrosurgical connection unit are to be connected to which electrosurgical channels may comprise information indicating which electrosurgical connection units are connected to an electrosurgical instrument and which of those are to be controlled or activated by the electrosurgical channel. Where there are multiple electrosurgical channels that can be transported via the electrosurgical network the information may further comprise information indicating which of the electrosurgical instruments are to be controlled or connected to which electrosurgical channel. Once the information has been received the method 1500 proceeds to block 1504.

At block 1504, the electrosurgical control unit 406 identifies the links (and/or portions thereof) of the electrosurgical network to be enabled to allow the desired electrosurgical connection units to be connected to the desired electrosurgical channels. Where there is only one electrosurgical channel that is transported via the electrosurgical network then links of the electrosurgical network are either enabled/active or disabled/inactive in their entirety based on whether they are required to connect the desired channels to the desired electrosurgical connection units. Using the system 700 of FIG. 7 as a first example, if there is a single electrosurgical channel that is to be connected to the electrosurgical connection unit of the second arm 402B the control unit may identify that only link 706 is to be active and the other links 704 and 708 can be inactive or disabled. Using the system 900 of a second example, if there is a single electrosurgical channel that is to be connected to the electrosurgical connection unit of the second arm 402B the control unit may identify that only links 906 and 902 need to be active and the other link can be inactive.

Where, however, the electrosurgical network can transport multiple electrosurgical channels the control unit may identify which links are to be active and further which portions of the links are to be active as not all of each link may be necessary. Using the system 1000 of FIG. 10 as an example, if there are two electrosurgical channels wherein the first electrosurgical channel is associated with the first two wires of each link and the second electrosurgical channel is associated with the remaining two wires of each link and the first electrosurgical connection unit of the first arm 402A is to be connected to the first electrosurgical channel and the electrosurgical connection unit of the second arm 402B is to be connected to the second electrosurgical channel then the electrosurgical control unit 406 may identify that all of link 1002 is to be active, only the first two wires of link 1004 are to be active and none of link 1006 are to be active.

Once the electrosurgical control unit 406 has identified the links (and/or portions thereof) of the electrosurgical network 404 to be enabled to allow the desired electrosurgical connection units to be connected to the desired electrosurgical channels the method 1500 proceeds to block 1506.

At block 1506, the electrosurgical control unit 406 transmits control signals to the electrosurgical output device (e.g. electrosurgical generator 414) and/or electrosurgical connection units 416 to cause the identified links (and/or portions thereof) to be enabled. For example, in the first single channel example above the electrosurgical control unit 406 may be configured to transmit a control signal to the electrosurgical distribution unit 710 to cause the link 706 to be active and the links 704, 708 to be inactive; and in the second single channel example above, the electrosurgical control unit 406 may be configured to transmit control signals to the electrosurgical connection unit 416 of the first arm 402A to cause the input port 418 to be connected to the second output port 912 which may result in the link 904 being disabled. In the multiple channel example above, the electrosurgical control unit 406 may be configured to transmit a control signal to the electrosurgical connection unit 416 of the second arm 402B to make a connection between the first two wires of the input port 418 and the first two wires of the output port 1012. The control signals that are transmitted by the electrosurgical control unit 406 may take any form that is understandable by the electrosurgical output device or the electrosurgical connection unit.

FIG. 16 illustrates a second example method 1600 which may be implemented by the electrosurgical control unit 406 to control which output ports 422 are connected to which electrosurgical channels. In this second example method 1600 the control unit is configured to cause an electrosurgical connection to be established between the electrosurgical output device and the output port of a selected combination of electrosurgical connection units by enabling an electrical connection between the input port and output port of selected electrosurgical connection units. The method 1600 begins at block 1602 where the electrosurgical control unit 406 receives information indicating which electrosurgical connection units are to be connected to which electrosurgical channels. Where there is only one electrosurgical channel that is transported via the electrosurgical network, the information indicating which electrosurgical connection units are to be connected to which electrosurgical channels may comprise information indicating which electrosurgical connection units are connected to an electrosurgical instrument and which of those are to be controlled or activated by the electrosurgical channel. Where there are multiple electrosurgical channels that can be transported via the electrosurgical network the information may further comprise information indicating which of the electrosurgical instruments are to be controlled or connected to which electrosurgical channel. Once the information has been received the method 1600 proceeds to block 1604.

At block 1604, the electrosurgical control unit 406 identifies the input port-output port connections that are to be established. Where there is only one electrosurgical channel that is transported via the electrosurgical network then the connection between the input port and the output port is either enabled or disabled in its entirety. Using the system 700 of FIG. 7 as a first example, if there is a single electrosurgical channel that is to be connected to the electrosurgical connection unit of the second arm 402B the control unit may identify that only the connection between the input port and the output port of the electrosurgical connection unit of the second arm 402B is to be enabled. Using the system 900 of a second example, if there is a single electrosurgical channel that is to be connected to the electrosurgical connection unit of the second arm 402B the control unit may identify that only that connection between the input port and the output port of the electrosurgical connection unit of the second arm 402B is to be enabled.

Where, however, the electrosurgical network can transport multiple electrosurgical channels the control unit may have to identify which portion of an input port is to be connected to the desired output port. Using the system 1000 of FIG. 10 as an example, if there are two electrosurgical channels wherein the first electrosurgical channel is associated with the first two wires of each link and the second electrosurgical channel is associated with the remaining two wires of each link and the first electrosurgical connection unit of the first arm 402A is to be connected to the first electrosurgical channel and the electrosurgical connection unit of the second arm 402B is to be connected to the second electrosurgical channel then the electrosurgical control unit 406 may identify that a connection between the first two wires of the input port 418 of the electrosurgical connection unit of the second arm 402B and the output port 422 is to be enabled and that a connection between the last two wires of the input port 418 of the electrosurgical connection unit 416 of the first arm 402A and the output port 422 is to be enabled.

Once the electrosurgical control unit 406 has identified the input port-output port connections to be enabled to allow the desired output ports to be connected to the desired electrosurgical channels the method 1600 proceeds to block 1606.

At block 1606, the electrosurgical control unit 406 transmits control signals to the electrosurgical connection units 416 to cause the identified input port-output port connections to be enabled. For example, in the first single channel example above the electrosurgical control unit 406 may be configured to transmit a control signal to the electrosurgical connection unit 416 of the second arm 402B to enable the connection between the input port 418 and the output port 422; and in the second single channel example above, the electrosurgical control unit 406 may be configured to transmit a control signals to the electrosurgical connection unit 416 of the second arm 402B to enable the connection between the input port 418 and the output port 422. In the multiple channel example above, the electrosurgical control unit 406 may be configured to transmit a control signal to the electrosurgical connection unit 416 of the second arm 402B to make a connection between the first two wires of the input port 418 and the output port 422 and transmit a control signal to the electrosurgical connection unit 416 of the first arm 402A to make a connection between the last two wires of the input port 418 and the output port 422. The control signals that are transmitted by the electrosurgical control unit 406 may take any form that is understandable by the electrosurgical connection units.

In yet another example method, which is not shown, the methods 1500 and 1600 of FIGS. 15 and 16 may be combined so that the electrosurgical control unit 406 generates control signals which cause selective links (and/or portions thereof) of the electrosurgical network to be enabled and which cause connections between the input port and output port of selected electrosurgical connection units to be established.

Figure 17:
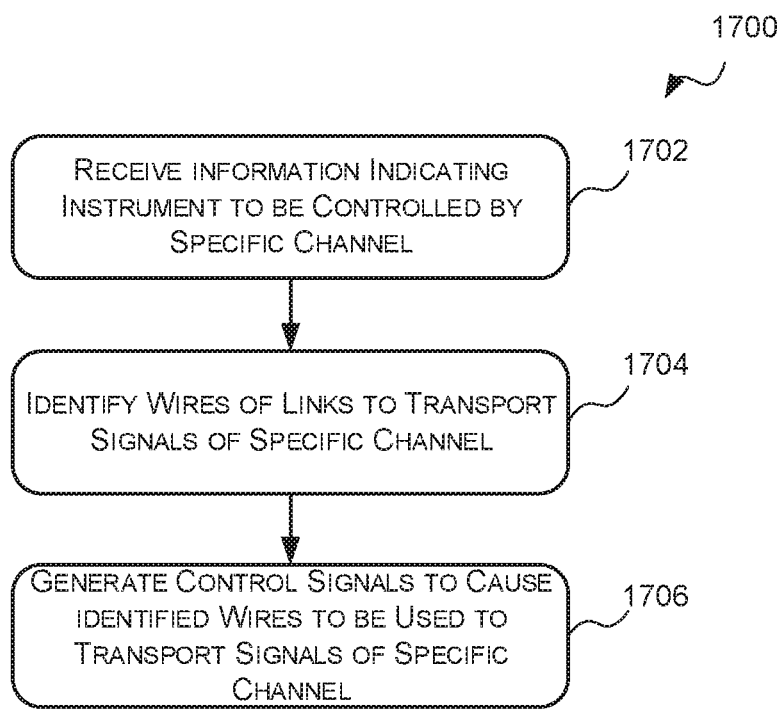
FIG. 17 is a flow diagram of a third example method to control which output ports of the electrosurgical connection units are connected to which electrosurgical channels.

Reference is now made to FIG. 17 which illustrates an example method 1700 which may be implemented by the electrosurgical control unit 406 to control the electrosurgical MUX 1434 and switching units 1452 of the system 1400 of FIG. 14 where multiple channels are dynamically mapped to the wires of the links of the electrosurgical network. The method 1700 begins at block 1702 where the electrosurgical control unit 406 receives information indicating that an electrosurgical instrument is to be controlled by a particular channel. The information may be received in response to an electrosurgical instrument being attached to the arm 402A, 402B and 402C. For example, in some cases when it has been detected (e.g. by the arm) that an electrosurgical instrument has been attached to the arm, the user may be asked to select which channel is to be used to control the electrosurgical instrument and then this information is provided to the control unit. Alternatively, the information may be received in response to the user triggering the generation of a driving electrosurgical signal to be provided to an electrosurgical instrument attached to an arm of the system. Once the information has been received the method 1700 proceeds to block 1704.

At block 1704, the electrosurgical control unit identifies wires of the electrosurgical link connected to the electrosurgical MUX 1434 which can be used to transport the electrosurgical signals associated with the identified electrosurgical channel through the electrosurgical network. This may comprise identifying the unused wires of the electrosurgical link connected to the electrosurgical MUX 1434 and selecting one or more of the unused wires to be allocated to the identified electrosurgical channel. As described above, the number of electrosurgical wires allocated to a channel is based on the number of electrosurgical signals of the channel that are to be transported through the electrosurgical network. In some cases, only one electrosurgical signal (the driving electrosurgical signal) is transported through the electrosurgical network for a monopolar electrosurgical channel and multiple electrosurgical signals (the driving electrosurgical signal and the return electrosurgical signal) are transported through the electrosurgical network for a bipolar electrosurgical channel. In these cases, only one wire is allocated to monopolar channels and two wires are allocated to bipolar channels. Once the electrosurgical control unit 406 has identified wires of the electrosurgical link to be allocated to the identified electrosurgical channel the method 1700 proceeds to block 1706.

At block 1706 the electrosurgical control unit 406 transmits a control signal or control signals to the electrosurgical MUX 1434 to cause the desired electrosurgical channel to be mapped to the identified wire(s) and the control unit transmits a control signal or control signals to the appropriate electrosurgical connection unit 416 to cause the identified wires of the input port 418 to be mapped to the appropriate output port 422, 1222. The control signals may have any suitable form that is understood by the electrosurgical MUX 1434 and the electrosurgical connection units 416.

Where the electrosurgical control unit 406 is unable to identify, at block 1704, the required number of unused wires to support an identified electrosurgical channel the electrosurgical control unit 406 may refuse the request. This may be because a number of the electrosurgical wires or conductors have already been allocated to one or more other electrosurgical channels. Whether or not this is likely to occur is dependent on the number of electrosurgical wires or conductors in each network link and the number of electrosurgical instruments that can be in-use concurrently. An electrosurgical system wherein each link of the electrosurgical network comprises four electrosurgical wires or conductors would support up to four monopolar electrosurgical channels simultaneously, two bipolar electrosurgical channels simultaneously, or one bipolar electrosurgical channels and two monopolar electrosurgical channels simultaneously. This would be sufficient for a single-surgeon system where the surgeon can control a maximum of two surgical instruments simultaneously. This may not, however, be sufficient for a dual surgeon system where each surgeon can control a maximum of two surgical instrument simultaneously, but presently this is a very unlikely scenario as the risk of four simultaneous driving electrosurgical signals interfering or cross-coupling in some way is quite high which could have significant implications for the patient.

Any of the electrosurgical connection units described above may also comprise an additional port (not shown) connectable to a patient electrode to receive a return electrosurgical signal from. The return electrosurgical signal received from the return electrode is then transmitted through the electrosurgical network 404 in the same manner as the return electrosurgical signal received from a bipolar electrosurgical instrument This allows the patient electrode to be connected to the electrosurgical connection unit, instead of the electrosurgical generator. This may be advantageous in situation where the electrosurgical generator is not close to the patient or is situated in an inconvenient location to reach via a cable. The additional port may be treated in the same manner as the corresponding output port 422 for that electrosurgical connection unit in any of the embodiments described above. Specifically, the additional port may be permanently connected to the input port 418 or switchable connected to the input port 418 as described above.

In some cases, to reduce the number of cables in the operating room or operating theatre, the same cables may be used for data communication (e.g. for transmitting control signals) between the devices (e.g. electrosurgical connection units, electrosurgical distribution devices, electrosurgical multiplexor, and the control unit) of the electrosurgical network and for transmitting/transporting electrosurgical signals between the devices of the electrosurgical network. For example, the devices of the electrosurgical network may be connected by cables that comprise a plurality of elements for transporting signals (e.g. wires, conductors, or optical fibres or combination thereof) wherein at least a portion of the elements in the cable are used for data communication (e.g. to transmit control signals from the electrosurgical control unit 406 to the electrosurgical connection units and/or the electrosurgical output devices) and at least a portion of the elements in the cable are used to transmit the electrosurgical signals of an electrosurgical channel. In these cases, the devices of the electrosurgical network (e.g. electrosurgical connection units, electrosurgical distribution devices, electrosurgical multiplexor and the electrosurgical control unit) may be connected using such cables so that any device can communicate with the electrosurgical control unit and that any device can be connected to the electrosurgical channel. Then an electrosurgical generator may be connected to an electrosurgical connection unit or any other device and the electrosurgical signals generated by that electrosurgical generator may be transmitted to any electrosurgical connection unit in the network.

Figure 18:
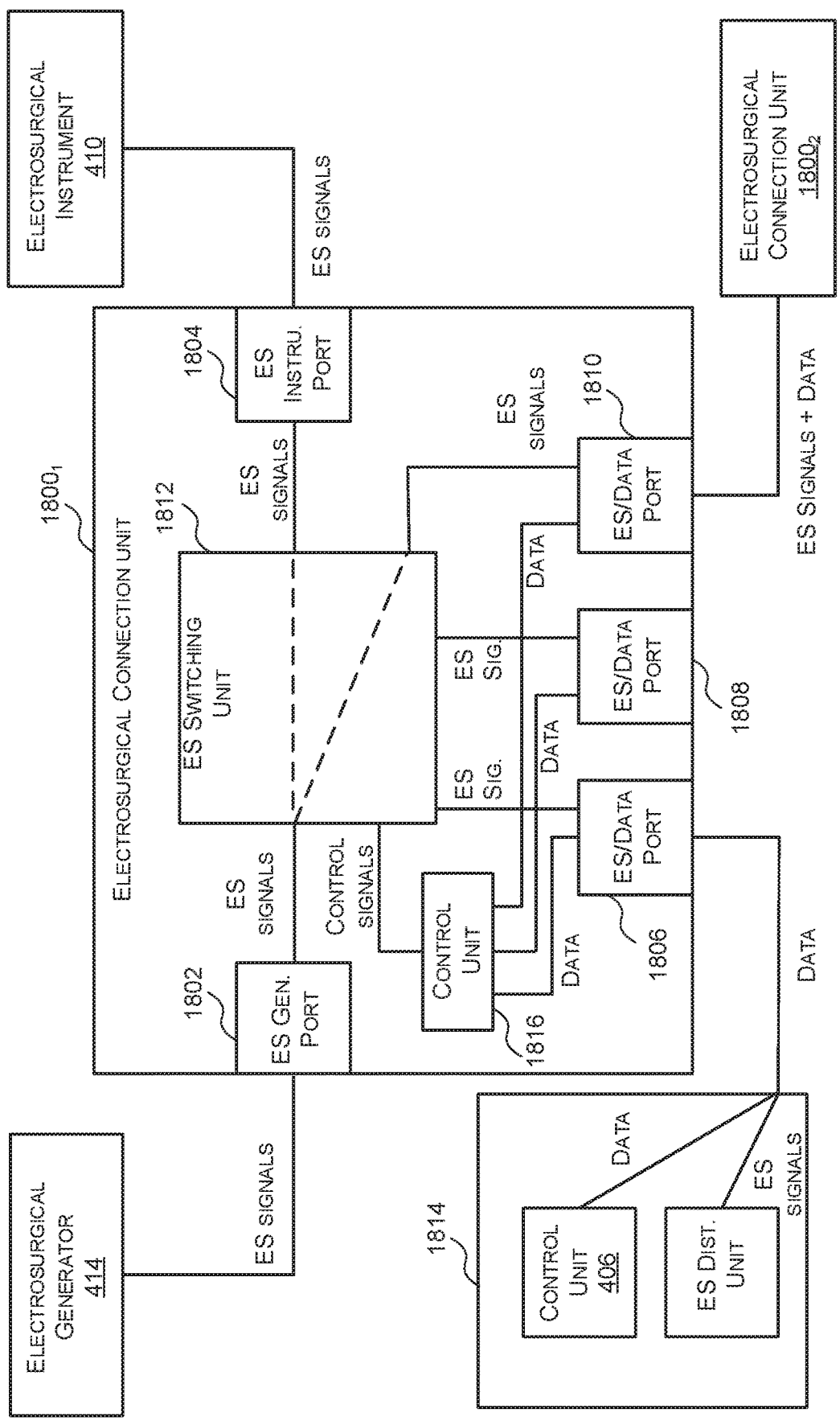
FIG. 18 is a schematic diagram of an example implementation of an electrosurgical connection unit in which data communications and electrosurgical signals are sent between devices of an electrosurgical network using the same cables and the electrosurgical generator is at a first example location in the electrosurgical network.
Figure 19:
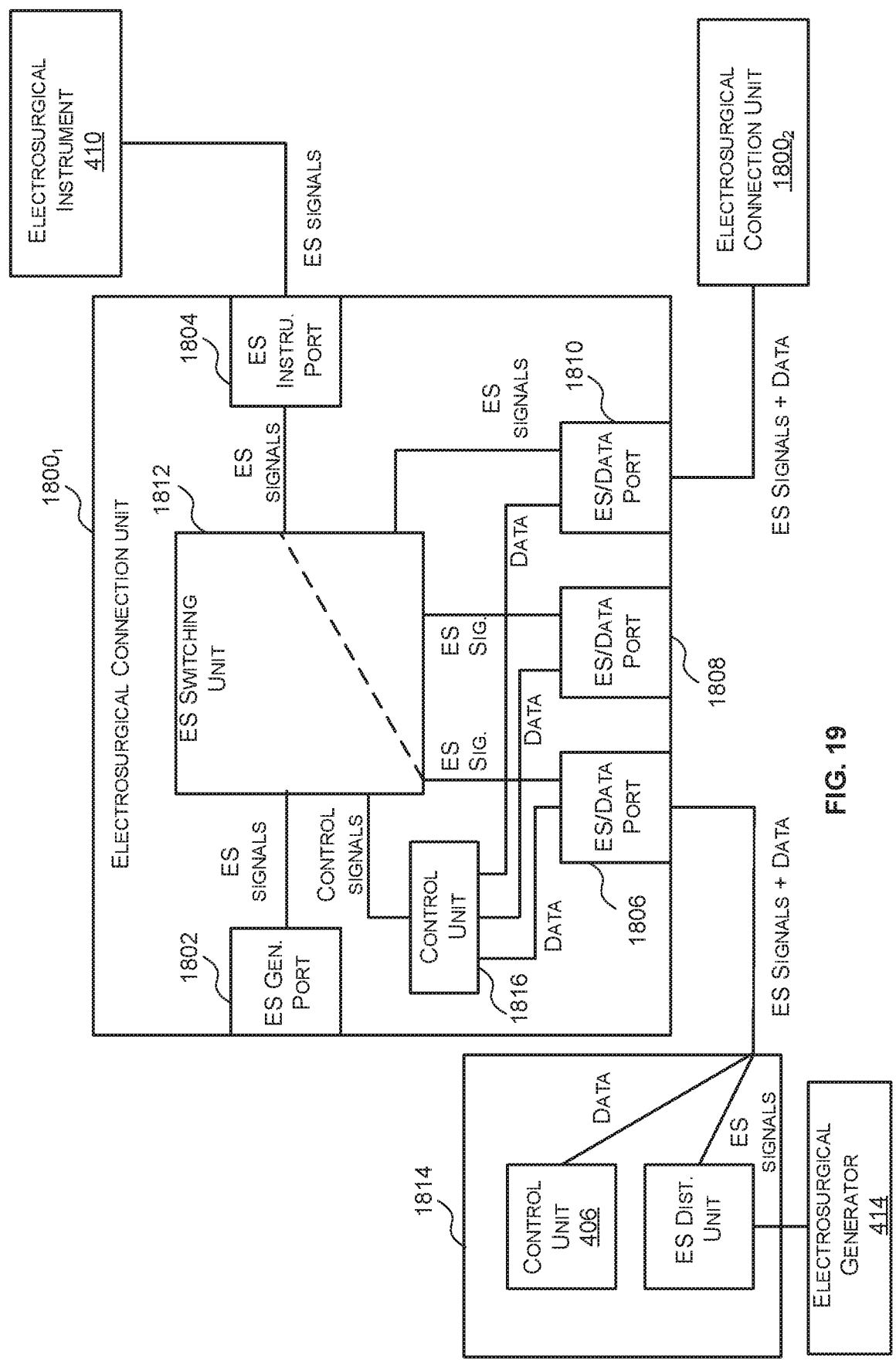
FIG. 19 is a schematic diagram of the electrosurgical connection unit wherein the electrosurgical generator is at a second example location in the electrosurgical network.
Figure 20:
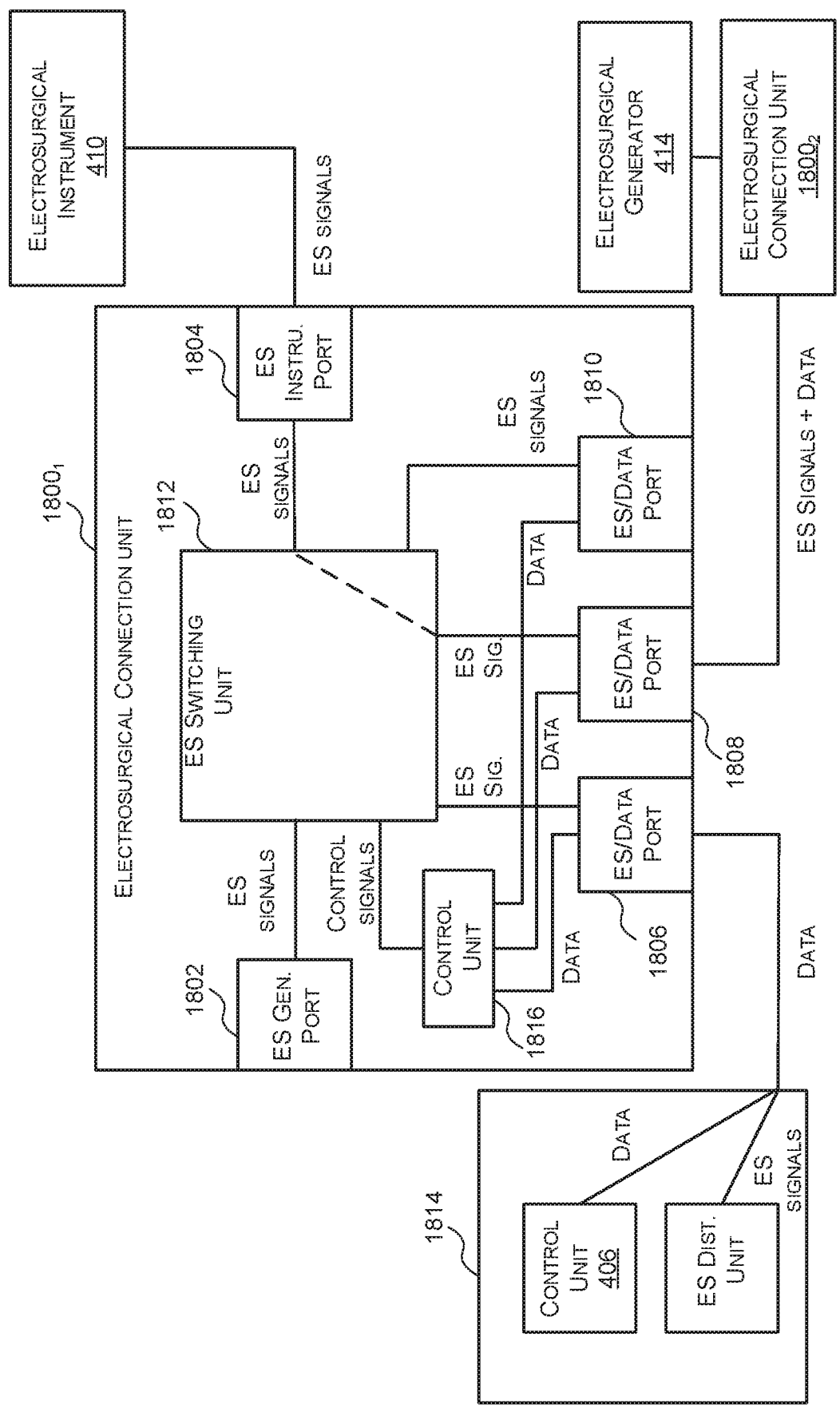
FIG. 20 is a schematic diagram of the electrosurgical connection unit wherein the electrosurgical generator is at a third example location in the electrosurgical network.

Reference is now made to FIGS. 18 to 20 which illustrate an example electrosurgical connection unit 1800₁ for use in a system wherein a single cable can be used for data transmission and electrosurgical signal transmission. The electrosurgical connection unit 1800₁ can be used to implement any of the electrosurgical connection units 416 described above. The electrosurgical connection unit 1800₁ of FIGS. 18 to 20 comprises an electrosurgical generator port 1802 which can receive an electrosurgical generator cable (i.e. a cable that is connected/connectable to an electrosurgical generator 414 over which electrosurgical signals may be transmitted); an electrosurgical instrument port 1804 which can receive an electrosurgical instrument cable (i.e. a cable that is connected/connectable to an electrosurgical instrument 410 over which electrosurgical signals can be transmitted); and a plurality of electrosurgical/data ports 1806, 1808, 1810 which can each receive an electrosurgical/data cable (i.e. a cable over which both data communications and electrosurgical signals may be transmitted). Each electrosurgical/data port 1806, 1808, 1810 may be used to connect the electrosurgical connection unit to another electrosurgical connection unit, an electrosurgical distribution unit, the electrosurgical control unit 406, or a combined electrosurgical control unit/electrosurgical distribution unit 1814. Although the electrosurgical connection unit 1800₁ of FIGS. 18 to 20 comprises three electrosurgical/data ports 1806, 1808, 1810 it will be evident to a person of skill in the art that this is an example only and that other example electrosurgical connection units may have a different number of electrosurgical/data ports.

In some cases, one or more of the electrosurgical generator port 1802, the electrosurgical instrument port 1804 and the electrosurgical/data ports 1806, 1808, 1810 may be keyed so that only a corresponding cable can be inserted therein. For example, the electrosurgical generator port 1802 may be keyed so that only an electrosurgical generator cable can be inserted therein.

The electrosurgical connection unit 1800 of FIGS. 18 to 20 also comprises an electrosurgical switching unit 1812 which is configured to controllably connect the electrosurgical elements of any port 1802, 1804, 1806, 1808, 1810 to any other port 1802, 1804, 1806, 1808, 1810 in accordance with control signals received from the electrosurgical control unit 406 so as to connect the electrosurgical generator 414 in the electrosurgical network to a particular electrosurgical instrument port 1804. The electrosurgical instrument port 1804 generally corresponds to the output port 422 of the electrosurgical connection units 416 described with reference to FIGS. 4 to 15. The electrosurgical switching unit 1812 may comprises one or more switches which can be controllably enabled or disabled to connected the electrosurgical elements of the ports accordingly. Electrically connecting the electrosurgical elements of a particular port with the electrosurgical elements of another port is referred to herein as establishing an electrosurgical connection between the ports. The specific ports which are electrosurgically connected is dependent on the location of the electrosurgical generator 414 in the network and the particular electrosurgical instrument port 1804 that is to be connected to the electrosurgical generator.

For example, in a first example shown in FIG. 18, the electrosurgical generator 414 is connected to the electrosurgical generator port 1802 of a first electrosurgical connection unit $1800_1$ and the first electrosurgical connection unit $1800_1$ is connected to a second electrosurgical connection unit $1800_2$ via the third electrosurgical/data port 1810. If in this example the electrosurgical instrument attached or connected to the first electrosurgical connection unit $1800_1$ is to be connected to the electrosurgical generator (e.g. is to be energised thereby) then the electrosurgical control unit 406 may transmit one or more control signals to the first electrosurgical connection unit $1800_1$ to cause the electrosurgical switching unit 1812 to electrosurgically connect the electrosurgical generator port 1802 to the electrosurgical instrument port 1804. In contrast, if instead the electrosurgical instrument attached to the second electrosurgical connection unit $1800_2$ is to be connected to the electrosurgical generator (e.g. is to be energised thereby) then the electrosurgical control unit 406 may transmit: one or more control signals to the first electrosurgical connection unit $1800_1$ to cause the electrosurgical switching unit 1812 to electrosurgically connect the electrosurgical generator port 1802 to the third electrosurgical/data port 1810; and one or more control signals to the second electrosurgical connection unit $1800_2$ to electrosurgically connect the electrosurgical/data port thereof connected to the first electrosurgical connection unit $1800_1$ to the electrosurgical instrument port thereof.

In another example shown in FIG. 19, the electrosurgical generator 414 is connected to a combined electrosurgical control unit and electrosurgical distribution unit 1814; the combined electrosurgical control unit and electrosurgical distribution unit 1814 is connected to the first electrosurgical connection unit $1800_1$ via the first electrosurgical/data port 1806; and the first electrosurgical connection unit $1800_1$ is connected to a second electrosurgical connection unit $1800_2$ via the third electrosurgical/data port 1810. If in this example the electrosurgical instrument attached or connected to the first electrosurgical connection unit is to be connected to the electrosurgical generator (e.g. is to be energised thereby) then the electrosurgical control unit 406 may transmit one or more control signals to the first electrosurgical connection unit $1800_1$ to cause the electrosurgical switching unit 1812 to electrosurgically connect the first electrosurgical/data port 1806 to the electrosurgical instrument port 1804. In contrast, if instead the electrosurgical instrument attached to the second electrosurgical connection unit $1800_2$ is to be connected to the electrosurgical generator (e.g. is to be energised thereby) then the electrosurgical control unit 406 may transmit: one or more control signals to the first electrosurgical connection unit $1800_1$ to cause the electrosurgical switching unit 1812 to electrosurgically connect the first electrosurgical/data port 1806 to the third electrosurgical/data port 1810; and one or more control signals to the second electrosurgical connection unit $1800_2$ to cause the electrosurgical switching unit thereof to electrosurgically connect the electrosurgical/data port thereof that is connected to the first electrosurgical connection unit $1800_1$ to the electrosurgical instrument port thereof.

In another example shown in FIG. 20, the electrosurgical generator 414 is connected to the second electrosurgical connection unit $1800_2$ (e.g. via the electrosurgical generator port thereof); and the first electrosurgical connection unit $1800_1$ is connected to the second electrosurgical connection unit $1800_2$ via the second electrosurgical/data port 1808. If in this example the electrosurgical instrument attached or connected to the first electrosurgical connection unit $1800_1$ is to be connected to the electrosurgical generator (e.g. is to be energised thereby) then the electrosurgical control unit 406 may transmit: one or more control signals to the second electrosurgical connection unit $1800_2$ to cause the electrosurgical switching unit thereof to electrosurgically connect the electrosurgical generator port thereof to the electrosurgical/data port thereof that is connected to the first electrosurgical connection unit; and one or more control signals to the first electrosurgical connection unit $1800_1$ to cause the electrosurgical switching unit 1812 to electrosurgically connect the second electrosurgical/data port 1808 to the electrosurgical instrument port 1804. In contrast, if instead the electrosurgical instrument attached to the second electrosurgical connection unit $1800_2$ is to be connected to the electrosurgical generator (e.g. is to be energised thereby) then the electrosurgical control unit 406 may transmit one or more control signals to the second electrosurgical connection unit $1800_2$ to cause the electrosurgical switching unit thereof to electrosurgically connect the electrosurgical generator port thereof to the electrosurgical instrument port thereof.

Since the electrosurgical connection unit $1800_1$, can, depending on the location of the electrosurgical generator in the network receive a driving electrosurgical signal from an electrosurgical generator on the electrosurgical generator port 1802 or on any of the electrosurgical/data ports 1806, 1808, 1810 then any of the electrosurgical generator port 1802 and the electrosurgical/data ports 1806, 1808, 1810 can act as the input port 418 of the electrosurgical connection units of FIGS. 4 to 14. For example, if the electrosurgical generator port 1802 is connected to the electrosurgical generator then the electrosurgical generator port acts as/becomes the input port 418. In contrast, if the electrosurgical generator port is not connected to the electrosurgical generator then one of the electrosurgical/data ports acts as/becomes the input port 418.

Similarly, depending on the location of the electrosurgical generator in the network one or more of the electrosurgical/data ports may act as/or become an output port 812, 912 of the electrosurgical connection units 416 of FIGS. 4 to 14. For example, if the electrosurgical generator port 1802 is connected to the electrosurgical generator and one of the electrosurgical/data ports is connected to another electrosurgical generator unit that electrosurgical/data port may act as, or become, the output port 912. Similarly, if the electrosurgical generator port 1802 is connected to the electrosurgical generator and one of the electrosurgical/data ports is connected to an electrosurgical distribution unit that electrosurgical/data port may act as, or become, the output port 812.

The electrosurgical connection unit $1800_1$ of FIGS. 18 to 20 also comprises an internal control unit 1816 which is configured to process the data communications (e.g. control signals) received via the data elements of the electrosurgical/data ports 1806, 1808, 1810. Specifically, the internal control unit 1816 is configured to process the data communications received via the data element of the electrosurgical/data ports 1806, 1808, 1810 to (i) control the electrosurgical switching unit 1812 (e.g. transmit control signals thereto); and (ii) allow communications between the devices that are not directly connected. For example, in the examples shown in FIGS. 18 to 20 the electrosurgical control unit 406 is connected to the first electrosurgical connection unit via the first electrosurgical/data port 1806 and the second electrosurgical connection unit is connected to the first electrosurgical connection unit via the second or third electrosurgical/data port 1808, 1810. In these examples the internal control unit 1816 may be configured to transmit data (e.g. control signals) directed to, or intended for, both the first and second electrosurgical connection units to the electrosurgical connection unit via the first electrosurgical/data port 1806. The internal control unit 1816 may then be configured to analyse the data received from the electrosurgical control unit 406 via the first electrosurgical/data port 1806 to determine if the data is intended for or directed to it. If the internal control unit 1816 determines that the data is intended for, or directed to, it then it may process that data, otherwise it may retransmit the data on the data elements of the other electrosurgical/data ports. For example, if the internal control unit 1816 of the first electrosurgical connection unit receives data (e.g. control signals) from the electrosurgical control unit 406 indicating that the electrosurgical generator port 1802 of the first electrosurgical connection unit is to be electrosurgically connected to the electrosurgical instrument port thereof the internal control unit 1816 may be configured to transmit one or more control signals to the electrosurgical switching unit 1812 to cause the electrosurgical switching unit 1812 to electrosurgically connect the electrosurgical generator port 1802 to the electrosurgical instrument port 1804. If, however, the internal control unit 1816 of the first electrosurgical connection unit receives data (e.g. control signals) from the electrosurgical control unit 406 intended for the second electrosurgical connection unit then the internal control unit 1816 may simply re-transmit that data (e.g. control signals) on the data elements of the other electrosurgical/data ports 1808, 1810.

The electrosurgical connection unit $1800_1$ of FIGS. 18 to 20 allows the electrosurgical connection units to be connected to the electrosurgical control unit 406 via the electrosurgical/data port in a star, daisy-chain or hybrid configuration (as described above) so that the electrosurgical control unit 406 can communicate with any and all of the electrosurgical connection units 416; and any of the electrosurgical instrument ports 1804 can be connected to the same electrosurgical channel regardless of where the electrosurgical generator of that electrosurgical channel is situated in the network. This allows the electrosurgical generator to be connected to any of the electrosurgical connection units or any electrosurgical distribution units in the network yet be electrically connected to the electrosurgical instrument port 1804 of any electrosurgical connection unit.

It will be evident to a person of skill in the art that the electrosurgical connection unit $1800_1$ of FIGS. 18-20 is an example only and that other example electrosurgical connection units may have additional and/or different components. For example, in cases where the electrosurgical generator is capable of communicating data via, and transmitting electrosurgical signals via, a common electrosurgical/data cable the electrosurgical connection unit may not have an electrosurgical generator port as the electrosurgical generator may be connectable to an electrosurgical/data port.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

The invention claimed is:

1. An electrosurgical system comprising:
a plurality of electrosurgical connection units, each electrosurgical connection unit comprising an input port connectable to an electrosurgical channel and an output port connectable to an electrosurgical instrument, the electrosurgical connection unit configured to connect the input port to the output port;
an electrosurgical network comprising a plurality of electrosurgical links that connect the input ports of the electrosurgical connection units to the electrosurgical channel; and
a control unit configured to:
receive information from a device indicating that the device has detected an electrosurgical generator connected to the electrosurgical channel, the device being one of the electrosurgical connection units and an electrosurgical output device connected to the electrosurgical channel;
determine a topological location of the electrosurgical generator in the electrosurgical network based on the received information; and
transmit one or more control signals to the electrosurgical connection units and/or one or more electrosurgical output devices connected to the electrosurgical channel to cause the output port of a selected combination of electrosurgical connection units to be connected to the electrosurgical channel based on the determined topological location of the electrosurgical generator.

2. The electrosurgical system of claim 1, wherein each electrosurgical connection unit comprises an electrosurgical generator cable detection unit configured to detect when an electrosurgical generator cable has been inserted in the electrosurgical connection unit, and in response to detecting that an electrosurgical generator cable has been inserted in the electrosurgical connection unit notify the control unit of the detection.

3. The electrosurgical system of claim 2, wherein the electrosurgical generator cable detection unit comprises at least one of a mechanical sensor, an electrical sensor, an optical sensor and a magnetic sensor configured to detect when an electrosurgical generator cable has been inserted in the electrosurgical connection unit.

4. The electrosurgical system of claim 2, wherein each of the electrosurgical connection units is configured to notify the control unit of a detection by, modifying a message received from the control unit to indicate the detection and transmitting the modified message to the control unit.

5. The electrosurgical system of claim 1, wherein the input port of each electrosurgical connection unit comprises a driving electrosurgical signal detection unit configured to, when operating in a test mode, detect when a driving electrosurgical signal is received on the input port, and in response to detecting that a driving electrosurgical signal has been detected on the input port notify the control unit of the detection.

6. The electrosurgical system of claim 1, wherein the electrosurgical generator is configured to detect when the electrosurgical generator is connected to the electrosurgical channel and in response to detecting that the electrosurgical generator is connected to the electrosurgical channel notify the control unit of the detection along with information indicating the topological location of the electrosurgical generator in the electrosurgical network.

7. The electrosurgical system of claim 1, wherein the one or more control signals transmitted by the control unit cause a selected combination of electrosurgical links to be active and all other electrosurgical links to be inactive.

8. The electrosurgical system of claim 1, further comprising a second electrosurgical network comprising a plurality of electrosurgical links connecting the input ports of the electrosurgical connection units to a second electrosurgical channel.

9. The electrosurgical system of claim 8, wherein the electrosurgical channel and the second electrosurgical channel are driven by a same electrosurgical generator; or the electrosurgical channel and the second electrosurgical channel are driven by different electrosurgical generators.

10. The electrosurgical system of claim 8, wherein at least one of the electrosurgical connection units further comprises a second output port and the at least one electrosurgical connection unit is configured to connect the electrosurgical channel to the output port and to connect the second electrosurgical channel to the second output port.

11. The electrosurgical system of claim 8, wherein at least one of the electrosurgical connection units comprises a switching unit situated between the input port and the output port, and the switching unit is configured to dynamically connect the electrosurgical channel to the output port in response to a first control signal and dynamically connect the second electrosurgical channel to the output port in response to a second, different, control signal.

12. The electrosurgical system of claim 11, wherein the electrosurgical channel and the second electrosurgical channel are of a same type.

13. The electrosurgical system of claim 1, wherein each electrosurgical link of the electrosurgical network comprises a plurality of electrosurgical conductors; and the system further comprises an electrosurgical multiplexer configured to receive the electrosurgical channel and a second electrosurgical channel and dynamically connect one or more of the electrosurgical channel and the second electrosurgical channel to one or more of the electrosurgical conductors in response to a control signal.

14. The electrosurgical system of claim 13, wherein each electrosurgical connection unit comprises a switching unit situated between the input port and the output port, the switching unit configured to controllably connect one or more electrosurgical conductors of the electrosurgical links to the output port in response to a control signal.

15. The electrosurgical system of claim 14, wherein at least one of the electrosurgical connection units comprises a second output port and the switching unit of the at least one electrosurgical connection unit is configured to controllably connect one or more electrosurgical conductors of the electrosurgical links to the second output port in response to a control signal.

16. The electrosurgical system of claim 8, wherein one of the electrosurgical channel and the second electrosurgical channel is a bipolar electrosurgical channel and the other of the electrosurgical channel and the second electrosurgical channel is a monopolar electrosurgical channel.

17. The electrosurgical system of claim 8, wherein the electrosurgical channel and the second electrosurgical channel are both bipolar electrosurgical channels; or, wherein the electrosurgical channel and the second electrosurgical channel are both monopolar electrosurgical channels.

18. The electrosurgical system of claim 1, further comprising a plurality of robot arms, each robot arm comprising:
    an attachment structure for removably attaching a surgical instrument to the robot arm; and
    one of the electrosurgical connection units for connecting an electrosurgical instrument attached to the robot arm to the electrosurgical channel.

19. The electrosurgical system of claim 1, wherein each electrosurgical connection unit further comprises a switching unit situated between the input port and the output port, the switching unit configured to controllably connect the input port to the output port in response to a control signal.

20. The electrosurgical system of claim 1, wherein the control unit is configured to transmit one or more control signals to the electrosurgical connection units and/or the electrosurgical output device to cause the output port of only one electrosurgical connection unit to be connected to the electrosurgical channel.

* * * * *